(12) United States Patent
Kinoshita et al.

(10) Patent No.: US 11,234,603 B2
(45) Date of Patent: Feb. 1, 2022

(54) PULSE WAVE DETECTION DEVICE, BIOLOGICAL INFORMATION MEASUREMENT DEVICE, AND CONTROL METHOD FOR PULSE WAVE DETECTION DEVICE

(71) Applicant: OMRON HEALTHCARE CO., LTD., Kyoto (JP)

(72) Inventors: Hiroyuki Kinoshita, Muko (JP); Tsuyoshi Kitagawa, Muko (JP); Shingo Yamashita, Muko (JP); Toshihiko Ogura, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 550 days.

(21) Appl. No.: 16/158,994

(22) Filed: Oct. 12, 2018

(65) Prior Publication Data

US 2019/0046046 A1    Feb. 14, 2019

Related U.S. Application Data

(63) Continuation of application No. PCT/JP2017/014751, filed on Apr. 11, 2017.

(30) Foreign Application Priority Data

Apr. 15, 2016  (JP) .............................. JP2016-082068

(51) Int. Cl.
*A61B 5/02* (2006.01)
*A61B 5/022* (2006.01)
(Continued)

(52) U.S. Cl.
CPC ............ *A61B 5/022* (2013.01); *A61B 5/0225* (2013.01); *A61B 5/02108* (2013.01);
(Continued)

(58) Field of Classification Search
CPC . A61B 5/02108; A61B 5/022; A61B 5/02116; A61B 5/02438; A61B 5/02444; A61B 5/6843; A61B 5/6824; A61B 5/681
See application file for complete search history.

(56) References Cited

U.S. PATENT DOCUMENTS

| 4,784,152 A | 11/1988 | Shinoda et al. |
| 4,830,017 A | 5/1989 | Perry et al. |

(Continued)

FOREIGN PATENT DOCUMENTS

| JP | 63-275320 | 11/1988 |
| JP | 1-288228 | 11/1989 |

(Continued)

OTHER PUBLICATIONS

Endo Toshiyuki, English Translation of "Pulse wave detector", Nov. 20, 1989, Japanese Patent Office, Translation obtained from Japan Platform for Patent Information. (Year: 1989).*

(Continued)

*Primary Examiner* — Christian Jang
(74) *Attorney, Agent, or Firm* — Wenderoth, Lind & Ponack, L.L.P.

(57) ABSTRACT

A pulse wave detecting device includes a sensor section and a control unit. The sensor section is rotatable about a first axis and is rotatable about a second axis. The control unit determines a rotation angle about the first axis based on DC components of pressure detecting elements included in element rows. Then, in a state where the sensor section is controlled to the optimal pitch angle, the sensor section is pressed against the body surface, and a pulse wave is detected based on pressure signals detected by pressure detecting elements in this state, and vital information is calculated based on the detected pulse wave.

9 Claims, 13 Drawing Sheets

(51) Int. Cl.
  *A61B 5/0225* (2006.01)
  *A61B 5/00* (2006.01)
  *A61B 5/024* (2006.01)
  *A61B 5/021* (2006.01)

(52) U.S. Cl.
  CPC ...... *A61B 5/02116* (2013.01); *A61B 5/02444* (2013.01); *A61B 5/6824* (2013.01); *A61B 5/6843* (2013.01); *A61B 5/02141* (2013.01); *A61B 2560/0223* (2013.01); *A61B 2562/0247* (2013.01); *A61B 2562/04* (2013.01)

(56) References Cited

U.S. PATENT DOCUMENTS

| | | | |
|---|---|---|---|
| 5,119,822 A * | 6/1992 | Niwa | A61B 5/021 600/485 |
| 6,132,383 A | 10/2000 | Chesney et al. | |
| 9,028,418 B2 | 5/2015 | Parzy et al. | |
| 2004/0193061 A1* | 9/2004 | Sato | A61B 5/02 600/500 |
| 2017/0224228 A1* | 8/2017 | Kitagawa | A61B 5/742 |
| 2017/0367649 A1 | 12/2017 | Kitagawa et al. | |

FOREIGN PATENT DOCUMENTS

| | | | |
|---|---|---|---|
| JP | H01288228 A * | 11/1989 | ............... A61B 5/02 |
| JP | 11-19054 | 1/1999 | |
| JP | 2002-330932 | 11/2002 | |
| JP | 2005-046464 | 2/2005 | |
| JP | 2009-72407 | 4/2009 | |
| JP | 2010-220948 | 10/2010 | |
| JP | 2014-195500 | 10/2014 | |
| JP | 2016-87004 | 5/2016 | |
| JP | 2016-158767 | 9/2016 | |
| WO | 01/17425 | 3/2001 | |

OTHER PUBLICATIONS

Extended European Search Report dated Aug. 21, 2019 in corresponding European Patent Application No. 17782373.9.
Office Action dated Feb. 18, 2020 in corresponding Japanese Patent Application No. 2016-082068 with English-language translation.
Office Action dated Sep. 2, 2020 in corresponding Chinese Patent Application No. 201780023682.X, with English Translation.
International Search Report dated Jul. 4, 2017 in International (PCT) Application No. PCT/JP2017/014751.
Written Opinion International Searching Authority dated Jul. 4, 2017 in International (PCT) Application No. PCT/JP2017/014751.

* cited by examiner

PULSE WAVE DETECTION DEVICE, BIOLOGICAL INFORMATION MEASUREMENT DEVICE, AND CONTROL METHOD FOR PULSE WAVE DETECTION DEVICE

CROSS REFERENCE TO RELATED APPLICATIONS

This application is a continuation of PCT application No. PCT/JP2017/014751, which was filed on Apr. 11, 2017 based on Japanese Patent Application (No. 2016-082068) filed on Apr. 15, 2016, the contents of which are incorporated herein by reference.

BACKGROUND OF THE INVENTION

The present invention relates to a pulse wave detecting device, a vital information measuring device, a method for controlling a pulse wave detecting device, and a control program for a pulse wave detecting device.

There is a known vital information measuring device capable of measuring vital information such as the pulse, the heart rate or the blood pressure using information detected by a pressure sensor set in contact with a surface of a living body portion where an artery such as the radial artery of the wrist passes (see Patent Literature 1).

Patent Literature 1 discloses a vital information measuring device including a drive section that rotates a pressure sensor including a plurality of element rows each including a plurality of pressure detecting elements about an axis extending in a direction perpendicular to an arrangement direction of the plural element rows (i.e., a direction perpendicular to an artery). In this vital information measuring device, maximum amplitude values of pulse waves detected by the respective plural element rows are compared with one another to rotate the pressure sensor in such a manner that the amplitude values accord with one another.

Patent Literature 1: Japanese Patent Publication No. H01-288228

SUMMARY OF THE INVENTION

In order to detect an accurate pulse wave from an artery using each of a plurality of element rows arranged in a direction of extending the artery, it is preferred that the artery is pressed similarly by each of the plural element rows.

In the vital information measuring device described in Patent Literature 1, the pressure sensor is rotated in such a manner that the maximum amplitude values of pulse waves respectively detected by the plural element rows accord with one another, so as to accord the pressing states of the artery by the plural element rows with one another.

When the artery is started to be occluded on the peripheral side having high resistance prior to the center side, however, a reflected wave is caused accordingly, and the reflected wave is superimposed on a pressure signal detected by the element row disposed on the center side, which may cause an error in the amplitude value of a pulse wave.

Besides, even when a reflected wave is not caused, since the plural element rows press different portions of a living body, there is a possibility that a difference may be caused in the attenuation factor of the amplitude among pulse waves detected by the respective element rows due to a difference in the composition of a subcutaneous tissue of the pressed portion, or the like.

The vital information measuring device described in Patent Literature 1 does not take such a detection error of a pulse wave detected by a plurality of element rows into consideration.

The present invention was devised in consideration of the above-described circumstances, and an object is to provide a pulse wave detecting device capable improving pulse wave detection accuracy by flexibly changing a pressing state, toward a body surface, of a sensor section pressed against the body surface for use, a vital information measuring device, a control method for a pulse wave detecting device, and a control program for a pulse wave detecting device.

The pulse wave detecting device of the present invention, includes:

a sensor section that includes at least one pair of pressure detecting elements arranged in a direction perpendicular to a first direction;

a pressing section that presses the sensor section against a body surface of a living body in a state where the first direction crosses a direction of an artery extending below the body surface;

a rotation drive section that rotates the sensor section about an axis extending in the first direction;

a storage control section that stores, in a storage medium, pressure signals detected by the pressure detecting elements in a state where a rotation angle of the sensor section about the axis is controlled to a specific value and the sensor section is pressed against the body surface by the pressing section; and a rotation angle determining section that determines the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

The vital information measuring device of the present invention includes: the above-described pulse wave detecting device; and a vital information calculating section that calculates vital information based on the pressure signals stored in the storage medium.

The method for controlling the pulse wave detecting device of the present invention, the pulse wave detecting device including: a sensor section that includes at least one pair of pressure detecting elements arranged in a direction perpendicular to a first direction; a pressing section that presses the sensor section against a body surface of a living body in a state where the first direction crosses a direction of an artery extending below the body surface; and a rotation drive section that rotates the sensor section about an axis extending in the first direction, the method includes:

a storage control step of storing, in a storage medium, pressure signals detected by the pressure detecting elements in a state where a rotation angle of the sensor section about the axis is controlled to a specific value and the sensor section is pressed against the body surface by the pressing section; and a rotation angle determining step of determining the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

The control program for the pulse wave detecting device of the present invention, the pulse wave detecting device including: a sensor section that includes at least one pair of pressure detecting elements arranged in a direction perpendicular to a first direction; a pressing section that presses the sensor section against a body surface of a living body in a state where the first direction crosses a direction of an artery extending below the body surface; and a rotation drive section that rotates the sensor section about an axis extending in the first direction, the control program causes a computer to execute:

a storage control step of storing, in a storage medium, pressure signals detected by the pressure detecting elements in a state where a rotation angle of the sensor section about the axis is controlled to a specific value and the sensor section is pressed against the body surface by the pressing section; and a rotation angle determining step of determining the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

DETAILED DESCRIPTION OF EXEMPLIFIED EMBODIMENT

An embodiment of the present invention will now be described with reference to the accompanying drawings.

Figure 1:
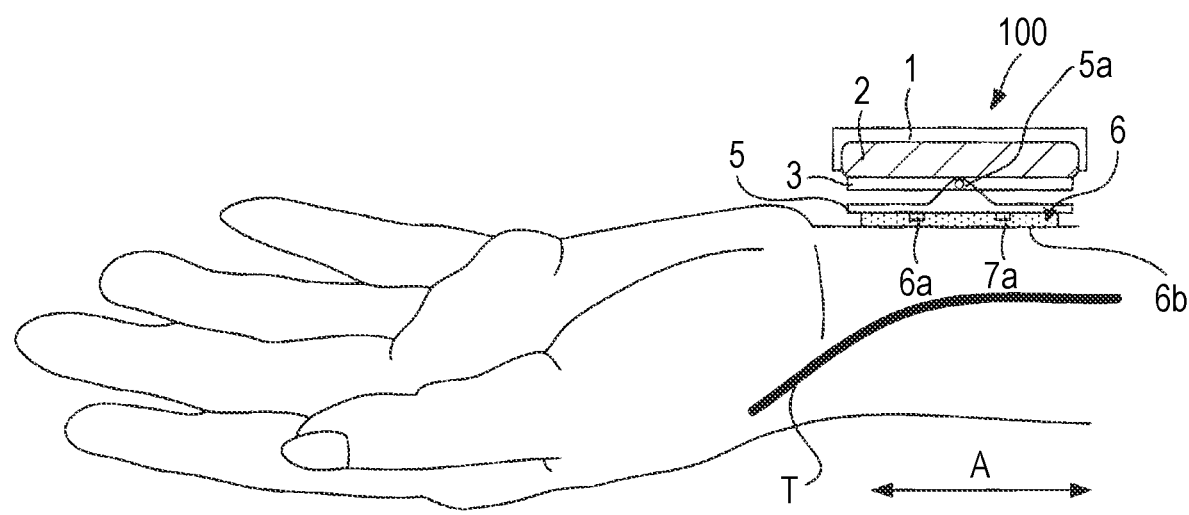
FIG. 1 is a schematic diagram illustrating the external structure of a pulse wave detection unit 100 of a vital information measuring device according to one embodiment of the present invention.

FIG. 1 is a schematic diagram illustrating an external structure of a pulse wave detection unit 100 of a vital information measuring device according to one embodiment of the present invention. The vital information measuring device of the present embodiment is used while worn, with a band not shown, on a living body portion (the left wrist of a user in an exemplified case of FIG. 1) in which an artery to be measured for vital information (the radial artery T in the exemplified case of FIG. 1) is present.

Figure 2:
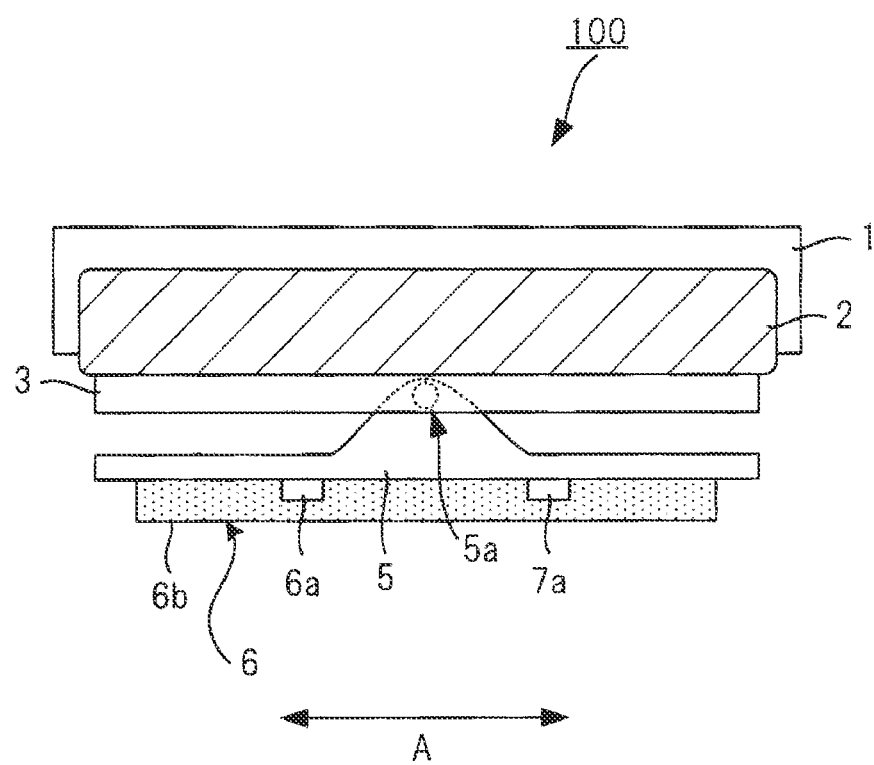
FIG. 2 is an enlarged view of the pulse wave detection unit 100 of FIG. 1.
Figure 3:
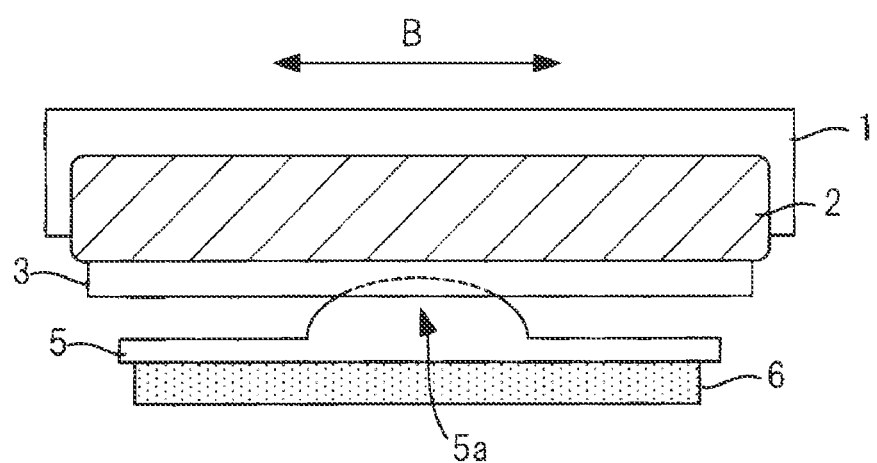
FIG. 3 is a diagram, taken from a side of the elbow of a user, of the pulse wave detection unit 100 in a worn state illustrated in FIG. 1.
Figure 4:
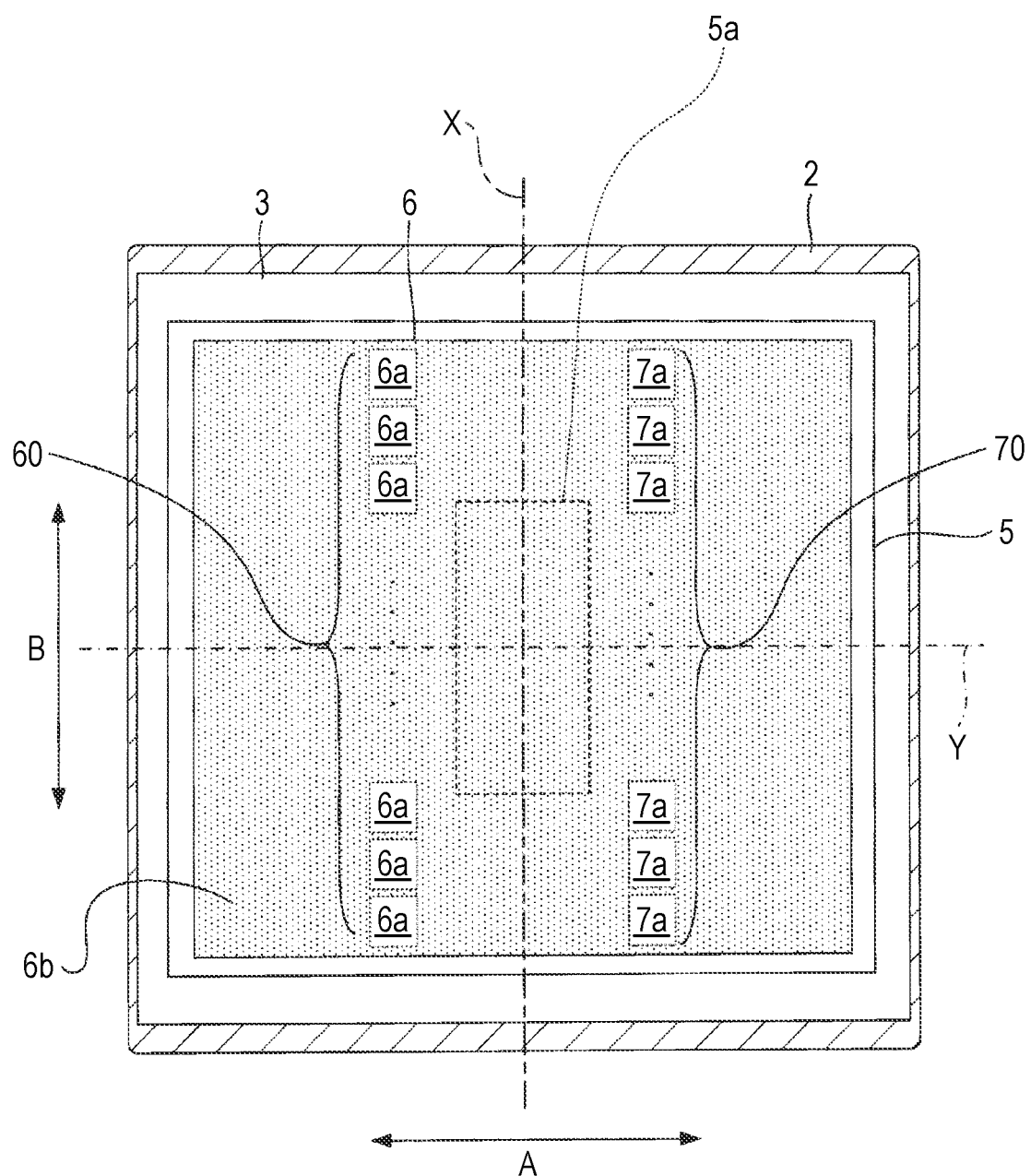
FIG. 4 is a diagram, taken from a side of a portion in contact with the wrist, of the pulse wave detection unit 100 in the worn state illustrated in FIG. 1.

FIG. 2 is an enlarged view of the pulse wave detection unit 100 of FIG. 1. FIG. 3 is a diagram, taken from a side of the elbow of the user, of the pulse wave detection unit 100 in a worn state illustrated in FIG. 1. FIG. 4 is a diagram, taken from a side of a portion in contact with the wrist, of the pulse wave detection unit 100 in the worn state illustrated in FIG. 1. It is noted that FIGS. 1 to 4 merely schematically illustrate the pulse wave detection unit 100, and do not limit dimensions and arrangement of respective components.

The pulse wave detection unit 100 includes a housing 1 including an air bag 2 therein, a plate section 3 corresponding to a plate-shaped member fixed on the air bag 3, a rotation section 5 supported on a biaxial rotation mechanism 5a rotatably against the plate section 3 around each of two axes, and a sensor section 6 provided on a surface of the rotation section 5 on the opposite side from the plate section 3.

The air bag 2 functions, in a state where the pulse wave detection unit 100 is worn on the wrist as illustrated in FIG. 1, as a pressing section for pressing a pressing surface 6b of the sensor section 6 against the body surface of a living body portion (the wrist). The pressing section can be any mechanism as long as it can press the sensor section 6 against the artery, and is not limited to one using an air bag.

The air bag 2 is controlled by a pump not shown for the amount of air held therein to move the plate section 3 fixed on the air bag 2 in a direction vertical to the surface of the plate section 3 (the surface on the side of the rotation section 5).

In the worn state illustrated in FIG. 1, the pressing surface 6b of the sensor section 6 included in the pulse wave detection unit 100 is in contact with the skin of the wrist of the user. In this state, the amount of air injected into the air bag 2 is increased to increase the internal pressure of the air bag 2, and hence the sensor section 6 is pressed against the body surface. Hereinafter, the description is made on the assumption that a pressing force applied by the sensor section 6 to the body surface is equivalent to the internal pressure of the air bag 2.

As illustrated in FIG. 4, the sensor section 6 includes an element row 60 including a plurality of pressure detecting elements 6a arranged in a direction B corresponding to a first direction, and an element row 70 including a plurality of pressure detecting elements 7a arranged in the direction B. The element row 60 and the element row 70 are arranged in a direction A perpendicular to the direction B. In the state where the pulse wave detection unit 100 is worn on the wrist, the element row 60 is disposed on a peripheral side, and the element row 70 is disposed on a center side.

Every pressure detecting element 6a forms a pair with a pressure detecting element 7a disposed in the same position in the direction B, and a plurality of such pairs are arranged in the direction B in the sensor section 6. As each of the pressure detecting elements 6a and the pressure detecting elements 7a, for example, any of a strain gauge resistance element, a semiconductor piezoresistance element and an electrostatic capacitance element is used.

The respective pressure detecting elements included in the element row 60 and the element row 70 are formed on the same plane surface, and the plane surface is protected by a protection member of a resin or the like. The plane surface having the pressure detecting elements thereon and the surface of the protection member protecting the plane surface are parallel to each other, and the surface of the protection member forms the pressing surface 6b.

Each of the pressure detecting elements 6a (7a) can detect a pressure vibration wave generated in the radial artery T and transmitted to the skin, namely, a pulse wave, when pressed against the radial artery T in such a manner that the arrangement direction crosses the radial artery T (at substantially right angles).

A distance in the arrangement direction between the pressure detecting elements 6a (7a) is set to be so sufficiently small that a necessary and sufficient number of elements can be disposed above the radial artery T. A length of the arrangement of the pressure detecting elements 6a (7a) is set to be larger than the diameter of the radial artery T by a necessary and sufficient size.

As illustrated in FIG. 4, the biaxial rotation mechanism 5a is a mechanism for rotating the rotation section 5 around each of a first axis X and a second axis Y, that is, two axes perpendicular to a pressing direction of the plate section 3 by the air bag 2.

The biaxial rotation mechanism 5a is rotatively driven by a rotation drive section 10 described later, so as to rotate the rotation section 5 around each of the first axis X and the second axis Y set on the surface of the plate section 3 to be perpendicular to each other.

The first axis X is an axis extending in the arrangement direction of the pressure detecting elements in the element row 60 or the element row 70 (the direction B). The first axis X is set between (in the exemplified case of FIG. 4, in the center between) the element row 60 and the element row 70 in the exemplified case of FIG. 4. The first axis X is in an arbitrary position in the direction A.

The second axis Y is an axis extending in the arrangement direction of the element row 60 and the element row 70 (the direction A). The second axis Y is set on a straight line equally dividing the element row 60 and the element row 70 in the exemplified case of FIG. 4. The second axis Y is in an arbitrary position in the direction B.

When the rotation section 5 is rotated around the first axis X, the sensor section 6 is rotated about the first axis X. Besides, when the rotation section 5 is rotated around the second axis Y, the sensor section 6 is rotated about the second axis Y.

Hereinafter, the rotation of the sensor section 6 about the first axis X is designated as pitch rotation. Besides, a rotation angle of the sensor section 6 about the first axis X is designated as a pitch angle. Furthermore, the rotation of the sensor section 6 about the second axis Y is designated as roll rotation. Besides, a rotation angle of the sensor section 6 about the second axis Y is designated as a roll angle.

The pitch angle is defined by an angle between a plane vertical to the pressing direction and the pressing surface 6b. In a state where the pressing surface 6b is vertical to the pressing direction, the pitch angle is 0 (zero) degree. It is assumed that a pitch angle obtained by pitch-rotating the sensor section 6 from this state to one direction (a positive direction) out of rotatable directions has a positive value, and that a pitch angle obtained by pitch-rotating the sensor section 6 in an opposite direction to the one direction (a negative direction) has a negative value.

Hereinafter, a direction of rotating the sensor section 6 from the state of the pitch angle of 0 (zero) degree in a direction in which the element row 60 comes closer to the body surface (a counterclockwise direction in FIG. 1) is defined as the positive direction of the pitch rotation, and a direction of rotating the sensor section 6 in a direction in which the element row 60 comes away from the body surface (a clockwise direction in FIG. 1) is defined as the negative direction of the pitch rotation.

The roll angle is defined by an angle between the plane vertical to the pressing direction and the pressing surface 6b. In a state where the pressing surface 6b is vertical to the pressing direction, the roll angle is 0 (zero) degree. It is assumed that a roll angle obtained by roll-rotating the sensor section 6 from this state to one direction (a positive direction) out of rotatable directions has a positive value, and that a roll angle obtained by roll-rotating the sensor section 6 in an opposite direction to the one direction (a negative direction) has a negative value.

Hereinafter, a direction of rotating the sensor section 6 from the state of the roll angle of 0 (zero) degree in the counterclockwise direction in FIG. 3 is defined as the positive direction of the roll rotation, and a direction of rotating the sensor section 6 from the state of the roll angle of 0 (zero) degree in the clockwise direction is defined as the negative direction of the roll rotation.

Each of the pitch angle and the roll angle can be controlled to a plurality of values.

Figure 5:
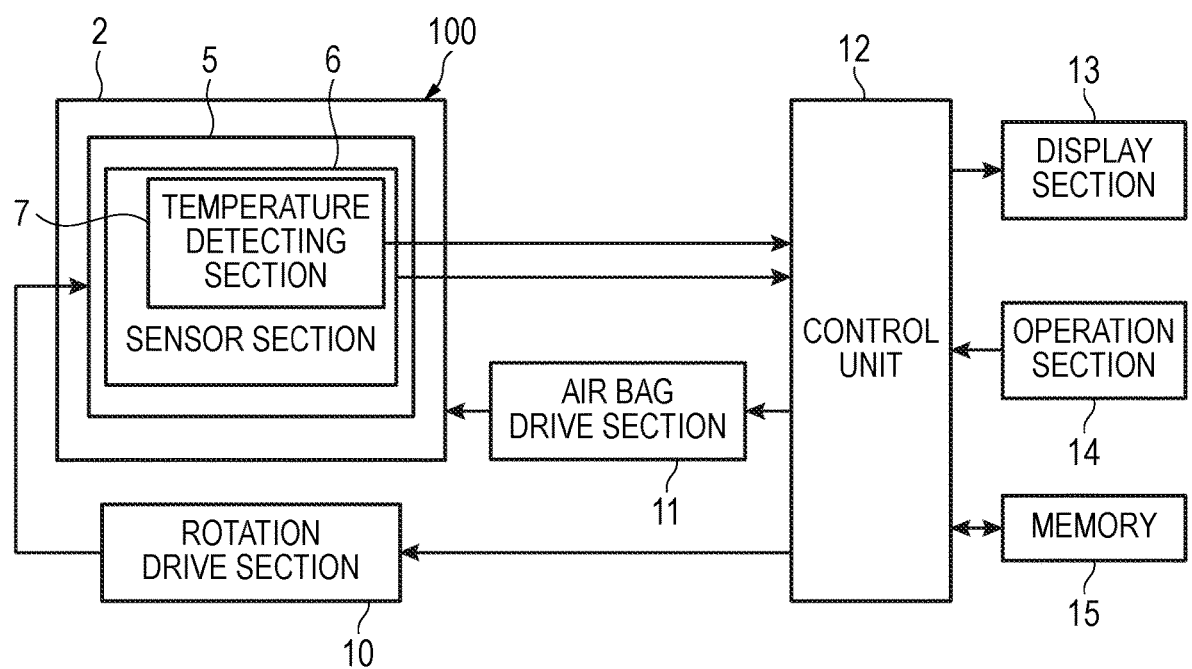
FIG. 5 is a diagram illustrating a block structure of the vital information measuring device of the present embodiment excluding the pulse wave detection unit 100.

FIG. 5 is a diagram illustrating a block structure of the vital information measuring device of the present embodiment excluding the pulse wave detection unit 100.

The vital information measuring device includes the pulse wave detection unit 100, the rotation drive section 10, an air bag drive section 11, a control unit 12 for integrally controlling the whole device, a display section 13, an operation section 14 and a memory 15.

The sensor section 6 of the pulse wave detection unit 100 is provided with a temperature detecting section 7. The temperature detecting section 7 detects a temperature in the vicinity of the pressure detecting elements 6a and 7a, and inputs the thus detected temperature information to the control unit 12.

The rotation drive section 10 is an actuator for driving the biaxial rotation mechanism 5a of the pulse wave detection unit 100. The rotation drive section 10 drives the biaxial rotation mechanism 5a in accordance with an instruction issued by the control unit 12, so as to rotate the sensor section 6 about the first axis X or rotate the sensor section 6 about the second axis Y.

The air bag drive section 11 includes a pump or the like, and controls the amount of air injected into the air bag 2 (the internal pressure of the air bag 2) in accordance with an instruction issued by the control unit 12.

The display section 13 is used for displaying various information including vital information, and includes, for example, a liquid crystal display or the like.

The operation section 14 is an interface for inputting an instruction signal to the control unit 12, and includes a button and the like for instructing start of various operations including measurement of vital information.

The memory 15 is a storage medium for storing a pressure signal detected by the sensor section 6 to be used for calculation of vital information and various information including the thus calculated vital information, and includes, for example, a flash memory or the like. The memory 15 may be a removable one.

The control unit 12 mainly includes a processor, and includes a ROM (read only memory) storing programs or the like to be executed by the processor, a RAM (random access memory) used as a work memory, and the like.

The programs include a control program. The ROM is a non-transitory storage medium from which a computer can read a program. The program stored in the ROM may be one downloaded from another equipment through a network to be stored therein.

The control unit 12 has the following functions through execution, by the processor, of the programs including the control program:

The control unit 12 controls the air bag drive section 11 for adjusting the amount of air held in the air bag 2, and thus, controls the pressing force applied by the sensor section 6 to the wrist. The control unit 12 thus functions as a pressing force control section.

The control unit 12 controls the rotation drive section 10 to rotate the sensor section 6, and thus, controls the pitch angle and the roll angle of the sensor section 6. The control unit 12 thus functions as a rotation control section.

The control unit 12 sets, on the basis of a temperature detected by the temperature detecting section 7, a reference level of a pressure signal (an output signal) detected by each of the pressure detecting elements 6a and 7a. Owing to the setting of the reference level, the level of the pressure signal detected by each of the pressure detecting elements 6a and 7a can be processed as a value based on the set reference level. The control unit 12 thus functions as a reference level setting section.

The control unit 12 controls the pitch angle of the sensor section 6 to a first value, controls the roll angle of the sensor section 6 to a second value, and stores, in the memory 15, a pressure signal detected by a pressure detecting element selected from the sensor section 6 in a state where the sensor section 6 is pressed against the body surface by the air bag 2 (which state is hereinafter referred to as the pulse wave measurement state). The control unit 12 thus functions as a storage control section.

The control unit 12 calculates vital information based on pressure signals detected in the pulse wave measurement state and stored in the memory 15, and stores the calculated vital information in the memory 15. The control unit 12 thus functions as a vital information calculating section.

The vital information may be any information as long as it can be calculated based on a pulse wave. The control unit 12 calculates, as the vital information, for example, blood pressure information such as an SBP (systolic blood pressure) and a DBP (diastolic blood pressure), pulse information such as a pulse count, or heart rate information such as a heart rate.

Incidentally, the vital information calculating section may be included another electronic equipment different from the vital information measuring device. In this case, the pressure signals stored in the memory 15 of the vital information measuring device are transmitted to the electronic equipment, and vital information is calculated and stored in the electronic equipment.

The control unit 12 determines the second value among a plurality of settable roll angles based on the pressure signals detected by the pressure detecting elements of the sensor section 6 in the state where the sensor section 6 is pressed against the body surface by the air bag 2, and controls the roll angle to the determined second value.

Then, the control unit 12 determines the first value among a plurality of settable pitch angles based on the pressure signals detected by one or plural pressure detecting elements of the sensor section 6 with the roll angle controlled to the second value. The control unit 12 thus functions as a rotation angle determining section.

The pulse wave detection unit 100, the rotation drive section 10, the air bag drive section 11 and functional blocks of the control unit 12 (the pressing force control section, the rotation control section, the reference level setting section, the storage control section and the rotation angle determining section) together construct a pulse wave detecting device.

Now, an operation of the vital information measuring device of the present embodiment will be described. The vital information measuring device of the present embodiment has a continuous blood pressure measurement mode in which the SBP and the DBP are calculated every heart rate to be displayed in the display section 13.

Figure 6:
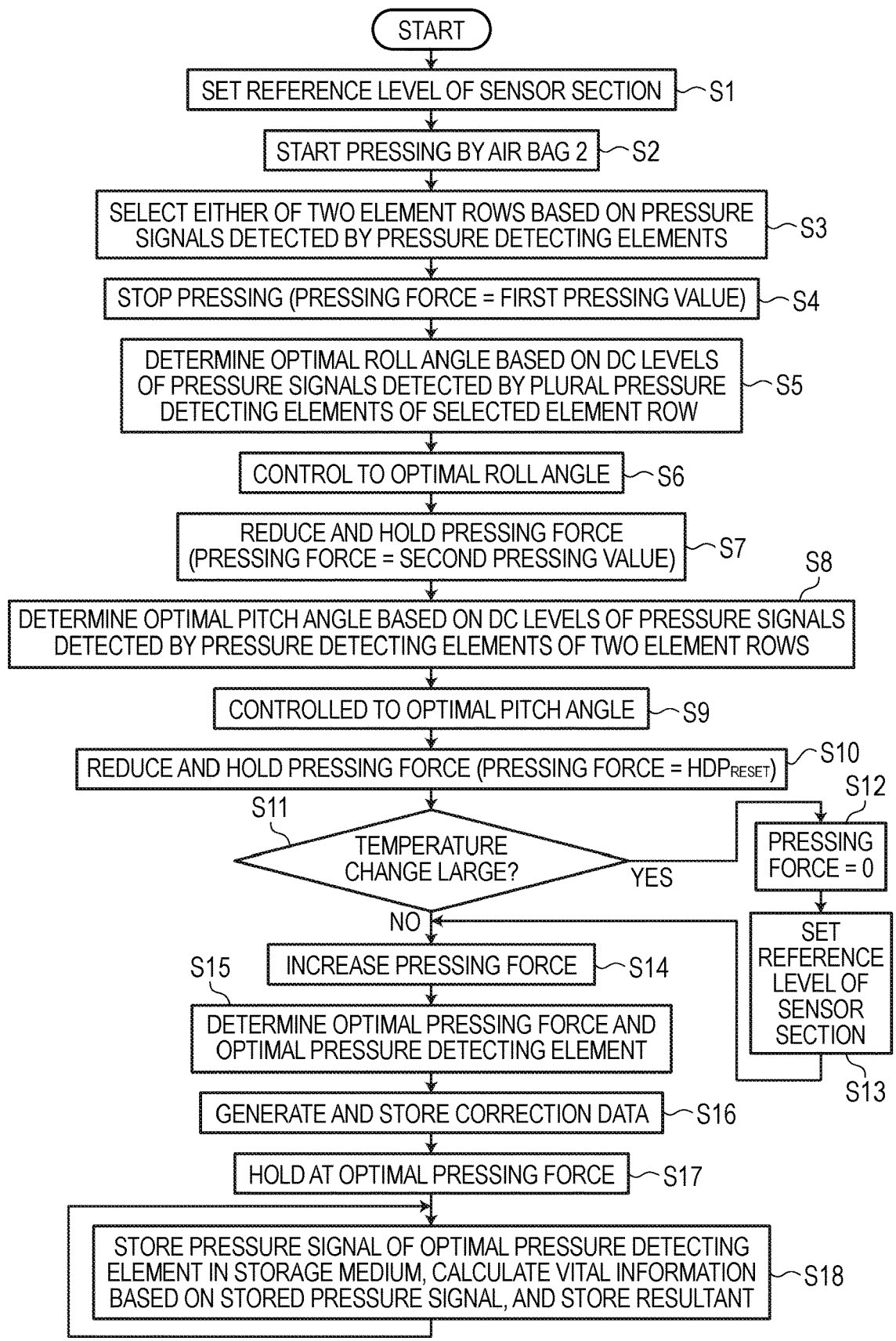
FIG. 6 is a flowchart used for explaining an operation in a continuous blood pressure measurement mode of the vital information measuring device of the present embodiment.

FIG. 6 is a flowchart used for explaining an operation in the continuous blood measurement mode of the vital information measuring device of the present embodiment.

Incidentally, in an initial state before a blood pressure measurement instruction is issued, it is assumed that the pitch angle and the roll angle are both set to, for example, 0 (zero) degree, and the pressing surface 6b is vertical to the pressing direction in the pulse wave detection unit 100.

Here, the state where the pitch angle and the roll angle are respectively set to 0 (zero) degree is defined as the initial state, which does not limit the present invention. For example, a state where the rotation drive section 10 roll-rotates or pitch-rotates the sensor section 6 so that, with the pulse wave detection unit 100 worn on the wrist, the pressing surface 6b can be placed in uniform contact with the skin in accordance with the shape of the wrist may be defined as the initial state.

When a blood pressure measurement instruction is issued, the control unit 12 obtains the temperature information detected by the temperature detecting section 7, and sets, based on the temperature information, the reference level of the pressure signal detected by each of the pressure detecting elements 6a and 7a of the sensor section 6 (step S1).

In the present embodiment, as each of the pressure detecting elements 6a and 7a included in the sensor section 6, an element in which a pressure signal (an offset level) detected with the pressing surface 6b in contact with nothing is varied depending on the temperature is used.

Therefore, based on the temperature detected by the temperature detecting section 7, the control unit 12 sets the reference level of the pressure signals detected by the pressure detecting elements 6a and 7a. Owing to the setting of the reference level, the levels of the pressure signals detected by the pressure detecting elements 6a and 7a are processed as values based on the set reference level.

Each of the pressure signals detected by the pressure detecting elements 6a and 7a includes a DC component independent of the heart rate and an AC component varied in accordance with the heart rate. A level of a rising point in a waveform of the pressure signal varied in accordance with the heart rate corresponds to the level of the DC component (the DC level). A difference between the rising point in the waveform of the pressure signal varied in accordance with the heart rate and a peak corresponds to the level of the AC component (the AC level).

After step S1, the control unit 12 controls the air bag drive section 11 to start injecting air into the air bag 2, so as to increase the pressing force applied by the sensor section 6 to the body surface (step S2).

The control unit 12 selects either the element row 60 or the element row 70 based on the pressure signal detected by each of the pressure detecting elements of the element row 60 and the element row 70 during the increase of the pressing force started in step S2 (step S3).

Here, the control unit 12 selects, from the element row 60 and the element row 70, one that has been able to more rapidly occlude the radial artery T during the increase. Now, the processing performed in step S3 will be described in detail with reference to FIG. 7.

Figure 7:
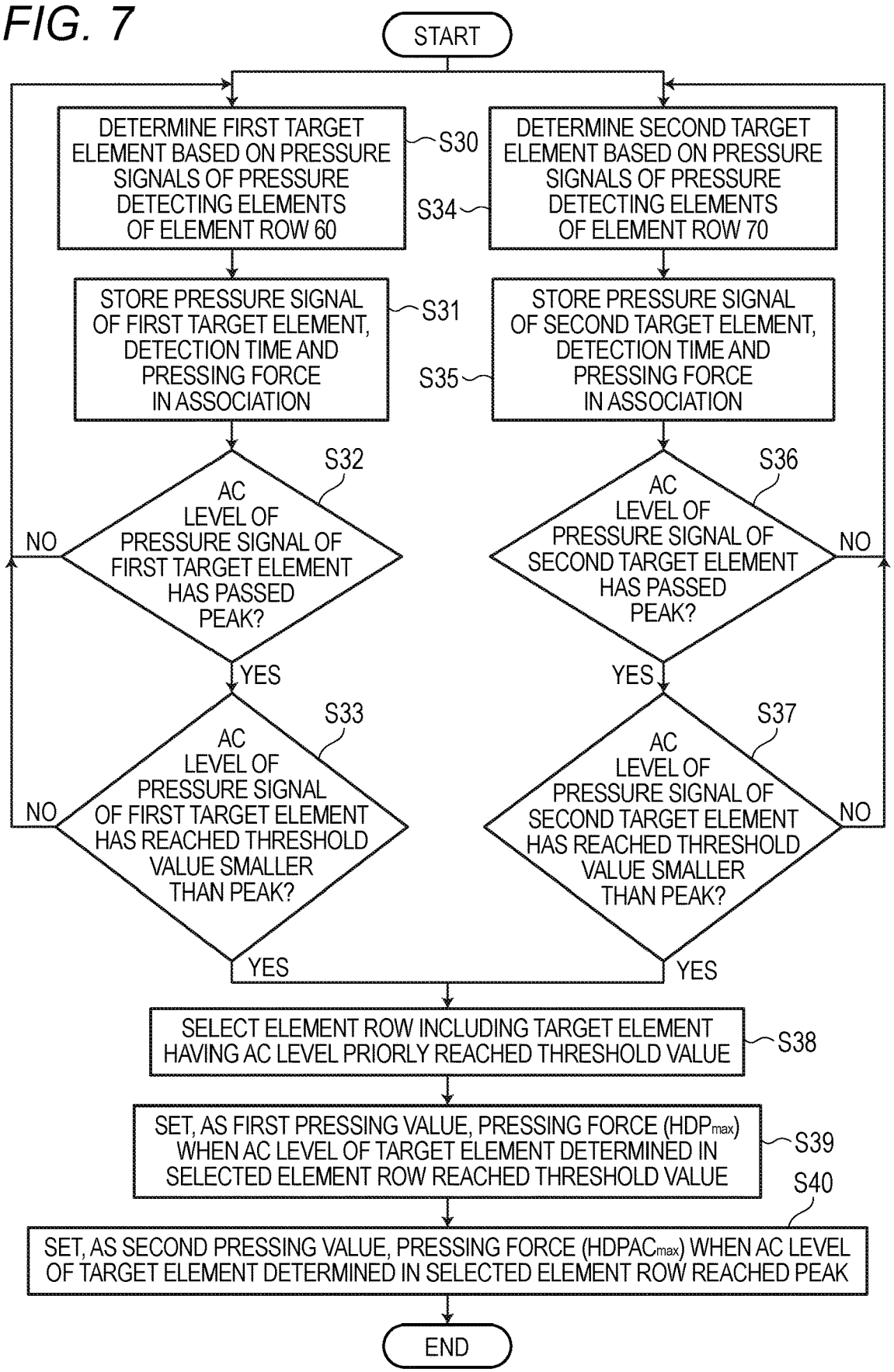
FIG. 7 is a flowchart used for explaining details of step S3 of FIG. 6.

FIG. 7 is a flowchart used for explaining details of step S3 of FIG. 6.

During the increase of the pressing force started in step S2, the control unit 12 determines, based on the pressure signal detected by each of the pressure detecting elements 6a of the element row 60, a target element (hereinafter referred to as the first target element) corresponding to one pressure detecting element positioned above the radial artery T out of all the pressure detecting elements 6a included in the element row 60 (step S30).

For example, the control unit 12 divides the pressure signal detected by each pressure detecting element 6a into the AC component and the DC component at arbitrary timing, and determines, as the first target element, a pressure detecting element 6a having an AC level equal to or more than an AC threshold value and having a DC level equal to or less than a DC threshold value.

Besides, when there are a plurality of pressure detecting elements 6a having an AC level equal to or more than the AC threshold value and having a DC level equal to or less than the DC threshold value, the control unit 12 determines, as the first target element, one having the maximum AC level and the minimum DC level out of the plural pressure detecting elements 6a.

The control unit 12 stores, in the RAM, an ID of the element row 60, an ID of the first target element determined in step S30, a pressure signal detected by the first target element, detection time of the pressure signal, and a pressing force applied by the air bag 2 at the detection time in association with one another (step S31).

After step S31, the control unit 12 determines, based on the pressure signal of the first target element at each detection time stored in the RAM, whether or not the AC level of the pressure signal detected by the first target element determined in step S30 has passed a peak (step S32).

Specifically, the control unit 12 compares a first AC level of a pressure signal corresponding to detection time immediately before the detection time of the pressure signal of the first target element determined in step S30 with a second AC level of the pressure signal of the first target element determined in step S30.

Then, when the second AC level is lower than the first AC level by a value equal to or more than a threshold value, the control unit 12 determines that the AC level of the pressure signal detected by the first target element determined in step S30 has passed the peak.

When the second AC level is not lower than the first AC level by the value equal to or more than the threshold value, or when merely one AC level of the pressure signal of the first target element is stored in the RAM, the control unit 12 determines that the AC level of the pressure signal detected by the first target element determined in step S30 has not passed the peak.

When it is determined as NO in step S32, the control unit 12 returns the processing to step S30.

When it is determined as YES in step S32, the control unit 12 determines whether or not the AC level of the pressure signal detected by the first target element determined in step S30 has reached an occlusion completion determination threshold value (hereinafter referred to as the first occlusion completion determination threshold value) smaller than the maximum value of the AC level of the pressure signal of the first target element stored in the RAM (step S33).

The first occlusion completion determination threshold value is set to a value obtained by multiplying the maximum value of the AC level of the pressure signal of the first target element stored in the RAM by a coefficient $\alpha$ that is larger than 0 and smaller than 1.

The first occlusion completion determination threshold value is a value used for determining whether or not the radial artery T has been occluded by the element row 60. The coefficient $\alpha$ is set to a value sufficient for assuring determination accuracy for this purpose. The coefficient $\alpha$ is set to, for example, 0.5.

When it is determined as NO in step S33, the control unit 12 returns the processing to step S30.

When it is determined as YES in step S33, the control unit 12 performs processing of step S38.

Concurrently with the processing of step S30 to step S33, the control unit 12 performs processing of step S34 to step S37.

In step S34, the control unit 12 determines a target element (hereinafter referred to as the second target element) corresponding to one pressure detecting element positioned above the radial artery T from all the pressure detecting elements 7a included in the element row 70 based on the pressure signal detected by each of the pressure detecting elements 7a of the element row 70 during the increase of the pressing force started in step S2.

A method for determining the second target element is the same as the method for determining the first target element. It is noted that the processing of step S34 is performed at the same time as the processing of step S30.

In step S35 following step S34, the control unit 12 stores, in the RAM, an ID of the element row 70, an ID of the second target element determined in step S34, a pressure signal detected by the second target element, detection time of the pressure signal and a pressing force applied by the air bag 2 at the detection time in association with one another.

In step S36 following step S35, the control unit 12 determines, based on the pressure signal of the second target element at each detection time stored in the RAM, whether or not the AC level of the pressure signal detected by the second target element determined in step S34 has passed a peak. A method for this determination is the same as that of step S32.

When it is determined as NO in step S36, the control unit 12 returns the processing to step S34.

When it is determined as YES in step S36, the control unit 12 determines whether or not the AC level of the pressure signal detected by the second target element determined in step S34 has reached an occlusion completion determination threshold value (hereinafter referred to as the second occlusion completion determination threshold value) smaller than the maximum value of the AC level of the pressure signal of the second target element stored in the RAM (step S37).

The second occlusion completion determination threshold value is set to a value obtained by multiplying the maximum value of the AC level of the pressure signal of the second target element stored in the RAM by the coefficient α.

When it is determined as NO in step S37, the control unit 12 returns the processing to step S34. When it is determined as YES in step S37, the control unit 12 performs processing of step S38.

In step S38, the control unit 12 selects, from the element row 60 and the element row 70, an element row including a target element whose AC level has reached the occlusion completion determination threshold value priorly.

In other words, when the detection time of the pressure signal of the first target element at which the AC level has reached the first occlusion completion determination threshold value is earlier than the detection time of the pressure signal of the second target element at which the AC level has reached the second occlusion completion determination threshold value, namely, when timing of determination of YES in step S33 is earlier than timing of determination of YES in step S37, the element row 60 is selected in step S38.

On the contrary, when the detection time of the pressure signal of the first target element at which the AC level has reached the first occlusion completion determination threshold value is later than the detection time of the pressure signal of the second target element at which the AC level has reached the second occlusion completion determination threshold value, namely, when the timing of determination of YES in step S37 is earlier than the timing of determination of YES in step S33, the element row 70 is selected in step S38.

The control unit 12 halts the processing of step S30 to step S37 when the element row is selected in step S38. The element row selected in step S38 will be hereinafter referred to as the selected element row.

Next, the control unit 12 sets, as a first pressing value, a pressing force ($HDP_{max}$) of the air bag 2 applied at the time when the AC level of the target element determined in the above-described selected element row stored in the RAM has reached the occlusion completion determination threshold value (step S39). Among the target elements determined in the selected element row, a target element whose AC level has reached the occlusion completion determination threshold value is sometimes referred to as the target element at the time of the occlusion completion.

Next, the control unit 12 sets, as a second pressing value, a pressing force ($HDP_{ACmax}$) of the air bag 2 applied at the time when the AC level of the target element determined in the above-described selected element row stored in the RAM has reached the maximum value (step S40).

Here, one of the element row 60 and the element row 70 is selected as the selected element row based on the pressure signals detected by the pressure detecting elements 6a and 7a, but it may be preliminarily determined which of the element row 60 and the element row 70 included in the sensor section 6 is to be selected as the selected row element.

For example, when the element row 60 is preliminarily set as the selected element row, the processing of step S34 to step S37 and the processing of step S38 can be omitted. In this case, when it is determined as YES in step S33, processing of step S39 and following step is performed.

Figure 8:
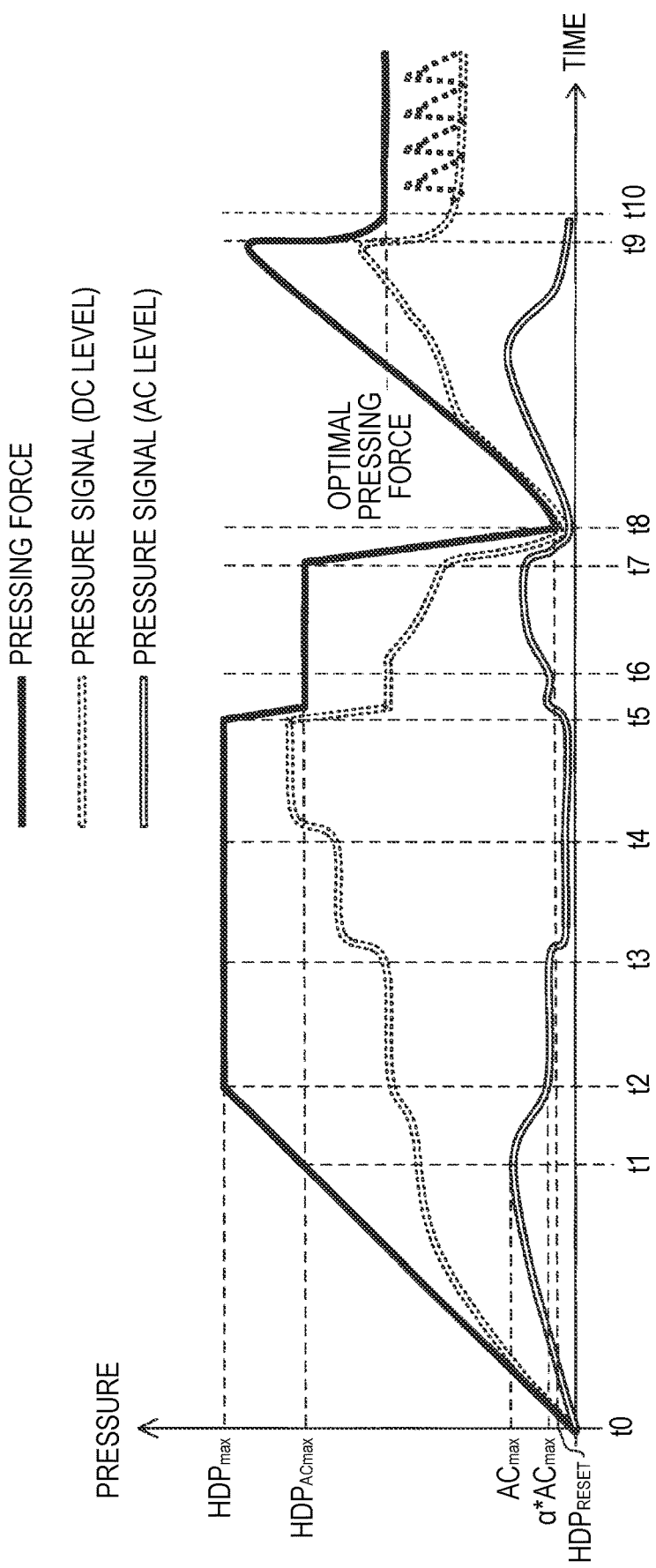
FIG. 8 is a diagram illustrating change in a pressure signal detected by a target element positioned above the radial artery in a selected element row selected in step S38 of FIG. 7.

FIG. 8 is a diagram illustrating change in the pressure signal detected by the target element determined in the selected element row selected in step S38 of FIG. 7. The abscissa indicates time and the ordinate indicates a pressure value. A pressure value at each time corresponds to the level of the pressure signal detected by the target element determined at that time.

When a blood pressure measurement instruction is issued, the reference level of the sensor section 6 is set before time t0 (step S1 of FIG. 6). Then, the pressing force increase is started at time t0 (step S2 of FIG. 6).

When the pressing force is started to increase, the AC level of the pressure signal detected by the target element reaches a peak ($AC_{max}$) at time t1, and reaches a value obtained by multiplying the $AC_{max}$ by the coefficient α (that is, 0.5 here) at time t2. Then, the selected element row is determined at time t2.

Incidentally, in a period between time t0 and time t2, the target element positioned above the radial artery T is determined at each time in each of the element rows 60 and 70.

At time t2, the pressing force ($HDP_{max}$) applied at time t2 is set as the first pressing value (step S39 of FIG. 7). Besides, at time t2, the pressing force ($HDP_{ACmax}$) applied at time t1 is set as the second pressing value (step S40 of FIG. 7).

Referring to FIG. 6 again, when the selected element row is determined by the processing of step S3, the control unit 12 controls the pressing force applied by the air bag 2 to the first pressing value set in step S39 of FIG. 7, and holds the pressing force in this state (step S4).

In the state where the pressing force is held at the first pressing value, the control unit 12 obtains the DC levels detected by the plural pressure detecting elements included in the selected element row, and on the basis of the thus obtained DC levels, determines a roll angle (hereinafter referred to as the optimal roll angle) to be employed for control at the time of generating correction data in step S14 and following steps, and at the time of continuous blood pressure measurement (step S5).

Figure 9:
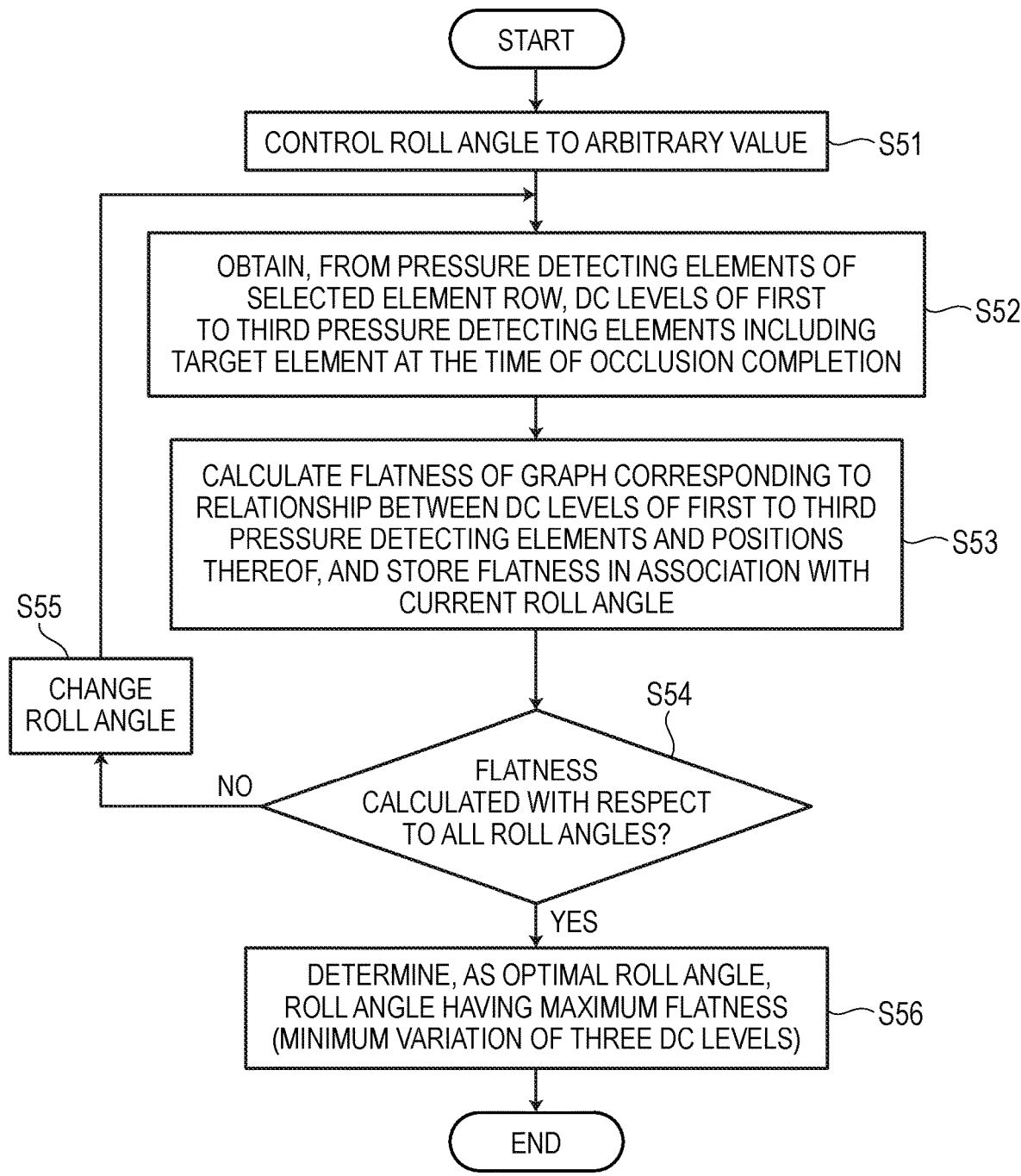
FIG. 9 is a flowchart used for explaining details of step S5 of FIG. 6.

FIG. 9 is a flowchart used for explaining details of step S5 of FIG. 6.

First, the control unit 12 controls the rotation drive section 10 to control the roll angle to an arbitrary value (step S51).

Next, the control unit 12 obtains the DC levels of pressure signals respectively detected by a first pressure detecting element (a target element determined at time t2 of FIG. 8) corresponding to the target element at the time of the occlusion completion among the pressure detecting elements of the selected element row, a second pressure detecting element adjacent on the radius side to the first pressure detecting element, and a third pressure detecting element adjacent on the ulna side to the first pressure detecting element (step S52).

Next, the control unit 12 calculates flatness of a graph corresponding to the relationship among the obtained three DC levels and the positions of the first to the third pressure detecting elements, and stores, in the RAM, the calculated flatness in association with the value of the roll angle currently employed by control (step S53).

For example, the control unit 12 obtains dispersion or standard deviation of the three DC levels, and regards the reciprocal of the obtained dispersion or standard deviation as the flatness. The flatness is defined as a numerical value corresponding to smallness of variation of these three DC levels.

Next, the control unit 12 determines whether or not the flatness has been calculated with respect to each of all the controllable roll angles (step S54).

When the flatness has not been calculated with respect to all the controllable roll angles (step S54: NO), the control unit 12 controls the rotation drive section 10 to make a change to a roll angle for which the flatness has not been calculated (step S55), and thereafter, the processing of step S52 and following steps is performed.

When the flatness has been calculated with respect to all the roll angles (step S54: YES), the control unit 12 determines, as the optimal roll angle, a roll angle in association with the maximum flatness (namely, the minimum variation of the DC levels) among the roll angles stored in the RAM through the processing of step S53 (step S56). Incidentally, it is preferable that the control unit 12 waits for a prescribed time period after controlling the roll angle to an arbitrary value in step S51, and obtains the DC levels of the pressure signals detected by the first to third pressure detecting elements of the selected element row at timing after the time period has elapsed. Immediately after changing the roll angle from one value to another value, a pressing posture of the sensor section 6 against the body surface is changed, and hence, there is a possibility that the blood flow is largely varied. Therefore, when the DC levels of the pressure signals are detected after waiting for a little after the control of the roll angle to an arbitrary value, the influence of such blood flow variation can be reduced.

Figure 10A:
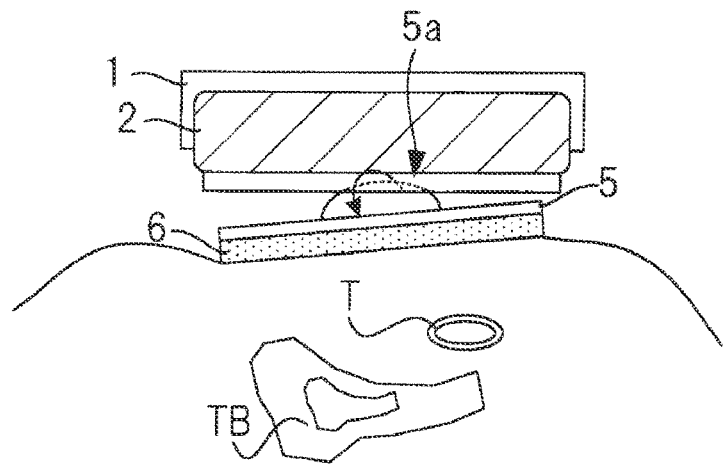
FIGS. 10A to 10C are diagrams illustrating states where a roll angle of the pulse wave detection unit 100 of FIG. 1 is controlled to three values.
Figure 10B:
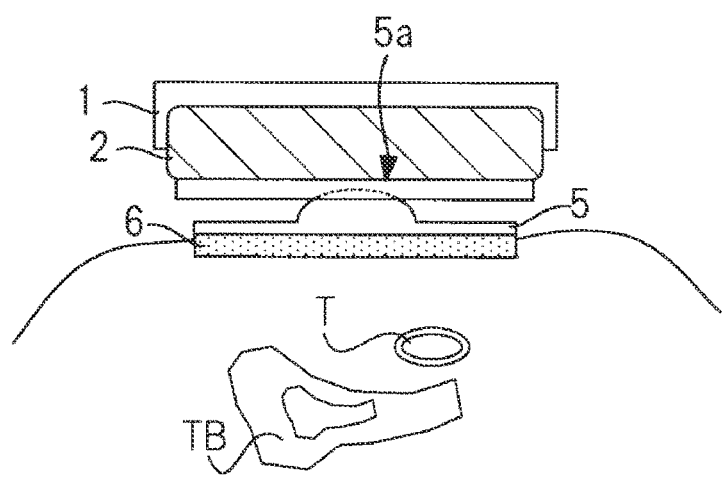
Figure 10C:
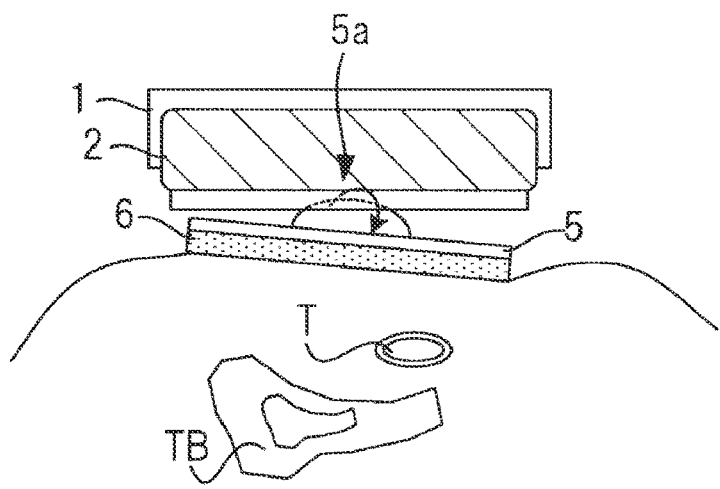

FIGS. 10A to 10C are diagrams illustrating states where the roll angle of the pulse wave detection unit 100 of FIG. 1 is controlled to three values. FIG. 10A illustrates a state where the roll angle is controlled to +θa degrees. FIG. 10B illustrates a state where the roll angle is controlled to 0 (zero) degree. FIG. 10C illustrates a state where the roll angle is controlled to −θa degrees. It is noted that θa is an arbitrary value.

Figure 11:
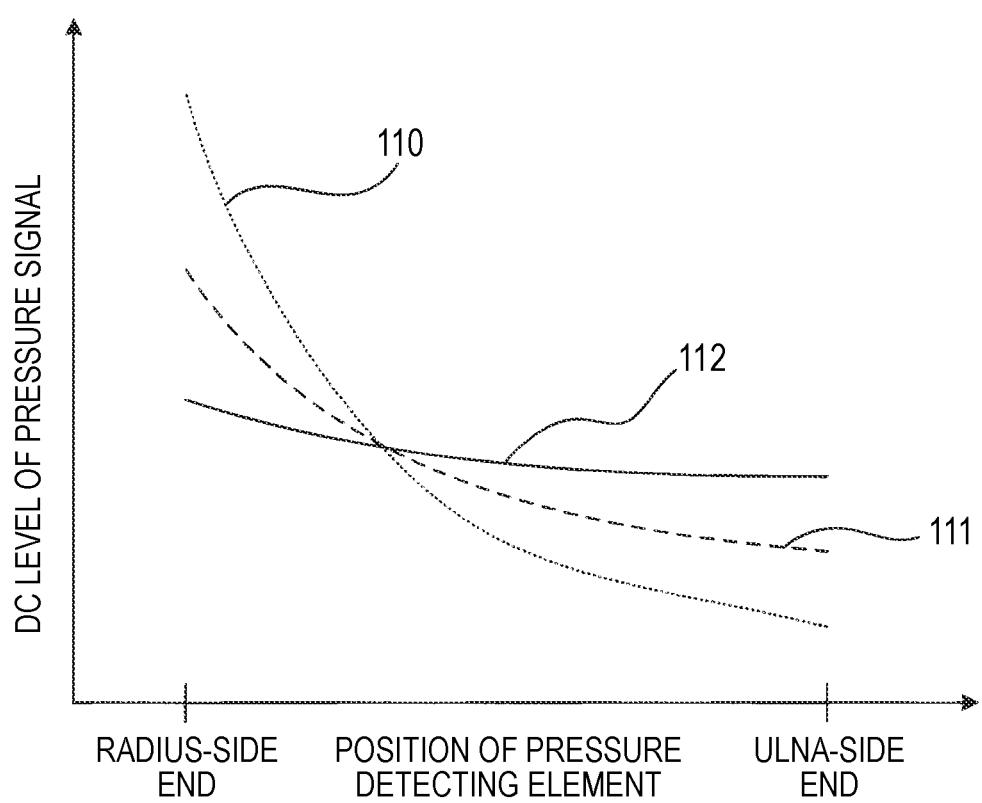
FIG. 11 is a graph illustrating a relationship between a DC level of a pressure signal detected by each pressure detecting element of the selected element row in a state where the roll angle is controlled as illustrated in FIGS. 10A to 10C and the position of the pressure detecting element.

FIG. 11 is a graph illustrating a relationship between a DC level of a pressure signal detected by each pressure detecting element of the selected element row with the roll angle controlled as illustrated in FIGS. 10A to 10C and the position of the pressure detecting element.

A curve 110 illustrated in FIG. 11 corresponds to an example of the DC level of the pressure signal detected by each pressure detecting element in the state of FIG. 10A. In the state of FIG. 10A, the end of the selected element row on the side of the radius TB is in a position close to the radius TB. Therefore, the curve 110 has a shape having a higher DC level in the end on the side of the radius TB.

A curve 111 illustrated in FIG. 11 corresponds to an example of the DC level of the pressure signal detected by each pressure detecting element in the state of FIG. 10B. In the state of FIG. 10B, a pressure from the radius TB is lower than in the state of FIG. 10A. Therefore, the inclination of the curve 111 is gentle as compared with the inclination of the curve 110.

A curve 112 illustrated in FIG. 11 corresponds to an example of the DC level of the pressure signal detected by each pressure detecting element in the state of FIG. 10C. In the state of FIG. 10C, the pressure from the radius TB is lower than in the state of FIG. 10B. Therefore, the inclination of the curve 112 is gentle as compared with the inclination of the curve 111, and has the highest flatness among the three curves 110, 111 and 112.

In this manner, when the DC level of the pressure signal detected by each pressure detecting element of the element row is observed, a distribution of the pressure from a hard tissue such as a bone or a tendon can be grasped.

Incidentally, the pressing force employed in determining the optimal roll angle preferably has a value that is not too large to cause a change in the curve such as the curves 110 to 112 by changing the roll angle. Besides, the pressing force employed in determining the optimal roll angle preferably has a value that is sufficiently large for detecting a pressure signal from a hard tissue (for sufficiently occluding the radial artery T).

In other words, when the coefficient α is set to an appropriate value, the pressing force employed in determining the optimal roll angle can be set to an appropriate magnitude, and hence, a distribution of the pressure from a hard tissue can be accurately grasped.

Each curve illustrated in FIG. 11 is formed by using DC levels of pressure signals detected by all the pressure detecting elements included in the selected element row. Below the selected element row, the radius, the radial artery and the tendon are present in this order.

Therefore, the shape of each curve illustrated in FIG. 11 can be mainly any of the following three patterns: A shape in which a pressure from the radius is strongly detected, and a DC level of a pressure detecting element, which is positioned closest to the radius (in the radius-side end) out of the pressure detecting elements included in the selected element row, is higher than a DC level of a pressure detecting element, which is positioned closest to the ulna (in the ulna-side end); a shape in which a pressure from a tendon is strongly detected, and the DC level of the pressure detecting element in the radius-side end is lower than the DC level of the pressure detecting element in the ulna-side end; and a flat shape.

Accordingly, in step S53 of FIG. 9, the control unit 12 may calculate the flatness of each curve illustrated in FIG. 11 with the pressure detecting element in the radius-side end among the pressure detecting elements included in the selected element row regarded as the second pressure detecting element, and with the pressure detecting element in the ulna-side end among the pressure detecting elements included in the selected element row regarded as the third pressure detecting element.

Alternatively, the control unit 12 may obtain, in step S52 of FIG. 9, the DC levels of the pressure signals detected by the two pressure detecting elements respectively positioned in the radius-side end and the ulna-side end of the selected element row, and may define, in step S53 of FIG. 9, a reciprocal of a difference between these two DC levels as the flatness of the curve illustrated in FIG. 11.

When a graph illustrating the relationship between the positions of the plural pressure detecting elements included in the selected element row and the DC levels detected by these is flatter, it means that the influence of the pressure from a hard tissue is smaller and the radial artery T can be pressed without being disturbed by the hard tissue.

In order to obtain a state where the radial artery T can be pressed without being disturbed by a hard tissue, the control unit 12 calculates the flatness with respect to each of all the controllable roll angles, and determines, as the optimal roll angle, a roll angle whose flatness thus calculated has the maximum value.

Incidentally, the control unit 12 may calculate the flatness based on variation in the DC level of pressure signals detected by all the pressure detecting elements included in the selected element row, so as to determine, as the optimal roll angle, a roll angle whose flatness thus calculated has the maximum value.

As described above, when the number of DC levels used for the calculation of the flatness is limited to two or three, computational complexity can be reduced. As a result, reduction of power consumption and fast determination of the optimal roll angle can be realized.

Besides, the control unit 12 determines the optimal roll angle based on the DC levels of the pressure signals detected by a plurality of pressure detecting elements of one element row selected from the element row 60 and the element row 70 in step S5 of FIG. 6, which does not limit the present invention. The control unit 12 may determine the optimal roll angle based on DC levels of pressure signals detected by the pressure detecting elements of each of the element row 60 and the element row 70.

For example, the control unit 12 obtains DC levels of the pressure signals detected by the plural pressure detecting elements in each of the element row 60 and the element row 70 in step S52 of FIG. 9.

Then, in step S53 of FIG. 9, the control unit 12 calculates the flatness based on the plural DC levels obtained with respect to the element row 60, stores the result in association with a roll angle currently employed by control, calculates the flatness based on the plural DC levels obtained with respect to the element row 70, and stores the result in association with the roll angle currently employed by control.

After calculating the flatness of each element row with respect to all the roll angles, the control unit 12 may determine the roll angle in association with the maximum flatness as the optimal roll angle in step S56 of FIG. 9.

Referring to FIG. 6 again, after step S5, the control unit 12 controls the roll angle of the sensor section 6 to the optimal roll angle determined in step S5 (step S6). Besides, the control unit 12 controls the pressing force applied by the air bag 2 to the second pressing value set in step S40 of FIG. 7, and holds the pressing force in this state (step S7).

The processing of step S5 to step S7 will be described with reference to FIG. 8. Incidentally, FIG. 8 illustrates exemplified operations performed when the roll angle can be controlled to the three values of 0 (zero) degree, +θ1 degrees and −θ1 degrees. It is noted that θ1 is an arbitrary value.

As illustrated in FIG. 8, the roll angle is controlled to 0 (zero) degree in a period from time t2 to time t3, and the flatness is calculated in this state. Subsequently, in a period from time t3 to time t4, the roll angle is controlled to +θ1 degrees, and the flatness is calculated in this state. Subsequently, in a period from time t4 to time t5, the roll angle is controlled to −θ1 degrees, and the flatness is calculated in this state.

In the exemplified case illustrated in FIG. 8, the flatness calculated in the state where the roll angle is controlled to 0 (zero) degree is the maximum (the optimal roll angle=0 (zero) degree). Therefore, the control unit 12 controls the roll angle of the sensor section 6 to 0 (zero) degree in a period from time t5 to time t6. Besides, the control unit 12 holds the pressing force at the second pressing value (HDP$_{ACmax}$) in the period from time t5 to time t6.

Incidentally, since the roll angle corresponding to the maximum flatness is 0 (zero) degree in the exemplified case of FIG. 8, the roll angle is changed from −θ1 degrees to 0 (zero) degree in the period from time t5 to time t6. If the flatness is maximum in the period from time t4 to time t5, however, there is no need to change the roll angle in the period from time t5 to time t6. In other words, the determination of the optimal roll angle and the control to the optimal roll angle may be simultaneously performed.

Referring to FIG. 6 again, after step S7, the control unit 12 determines a pitch angle to be employed by control at the time of the generation of correction data in step S14 and following steps and at the time of the continuous blood pressure measurement (hereinafter referred to as the optimal pitch angle) based on DC levels of the pressure signals detected by the plural pressure detecting elements included in each of the element row 60 and the element row 70 (step S8). In the exemplified case of FIG. 8, the processing of step S8 is performed in a period from time t6 to time t7.

Figure 12:
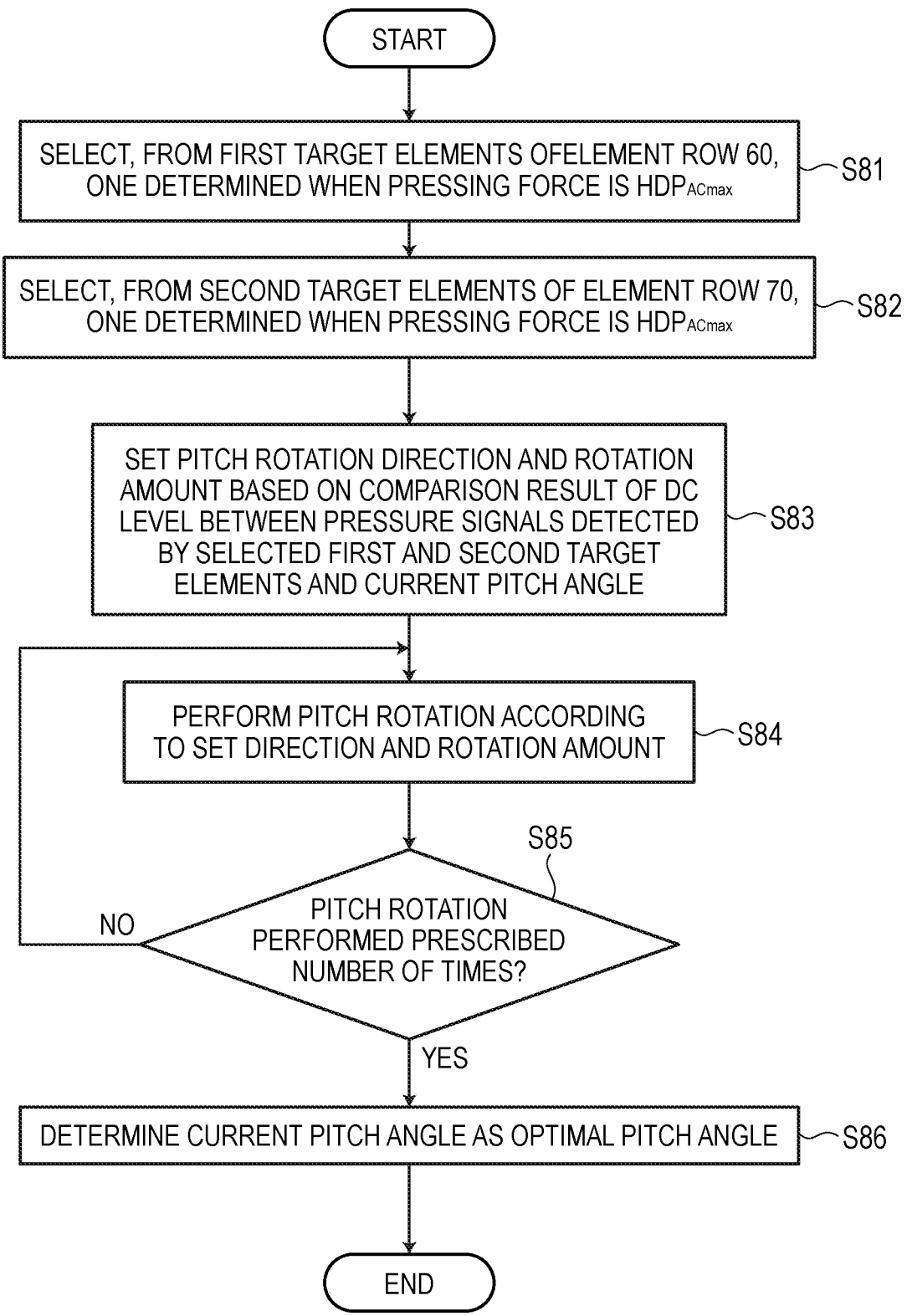
FIG. 12 is a flowchart used for explaining details of step S8 of FIG. 6.

FIG. 12 is a flowchart used for explaining details of step S8 of FIG. 6.

The control unit 12 selects, from the first target elements stored in the RAM in the process of step S30 to step S37 of FIG. 7, the first target element in association with the pressing force of the second value (HDP$_{ACmax}$) (step S81).

Besides, the control unit 12 selects, from the second target elements stored in the RAM in the process of step S30 to step S37 of FIG. 7, the second target element in association with the pressing force of the second value (HDP$_{ACmax}$) (step S82).

Incidentally, instead of performing step S81 and step S82, the control unit 12 may select one first target element positioned above the radial artery T based on the pressure signal detected by each of the pressure detecting elements 6a of the element row 60, and may select one second target element positioned above the radial artery T based on the pressure signal detected by each of the pressure detecting elements 7a of the element row 70.

After selecting the first target element and the second target element, the control unit 12 compares the DC level of the pressure signal detected by the selected first target element (hereinafter referred to as the peripheral-side DC level) with the DC level of the pressure signal detected by the selected second target element (hereinafter referred to as the center-side DC level), and sets the rotation direction and the rotation amount of the pitch rotation of the sensor section 6 based on the comparison result and the current pitch angle (step S83).

Specifically, when the peripheral-side DC level is lower than the center-side DC level, the control unit 12 sets the rotation direction to the positive direction (the counterclockwise direction in FIG. 1). Alternatively, when the center-side DC level is lower than the peripheral-side DC level, the control unit 12 sets the rotation direction to the negative direction (the clockwise direction in FIG. 1).

Besides, the control unit 12 sets the rotation amount to a half value of a difference between the absolute value of the current pitch angle of the sensor section 6 and the maximum value or the minimum value of the absolute value of the pitch angle that can be employed when the sensor section 6 is rotated in the rotation direction set in the above-described method from the current pitch angle.

It is assumed, for example, that the pitch angle is changeable by 5 degrees at the most in each of the positive direction and the negative direction from 0 (zero) degree. When the current pitch angle is 0 (zero) degree and the set rotation direction is the positive direction, the rotation amount is set to 2.5 degrees, that is, a half of a difference of 5 degrees, that is, the maximum value of the absolute value of the changeable pitch angle in the rotation from the current pitch angle in the positive direction, and 0 (zero) degree, that is, the current pitch angle.

Alternatively, when the current pitch angle is +2.5 degrees and the set rotation direction is the negative direction, the rotation amount is set to 1.25 degrees, that is, a half of a difference of 0 (zero) degree, that is, the minimum value of the absolute value of the changeable pitch angle in the rotation from the current pitch angle in the negative direction, and 2.5 degrees, that is, the current pitch angle.

Alternatively, when the current pitch angle is +2.5 degrees and the set rotation direction is the positive direction, the rotation amount is set to 1.25 degrees, that is, a half of a difference of 5 degrees, that is, the maximum value of the absolute value of the changeable pitch angle in the rotation from the current pitch angle in the positive direction, and 2.5 degrees, that is, the current pitch angle.

Then, the control unit 12 pitch-rotates the sensor section 6 in the set rotation direction correspondingly to the set rotation amount (step S84).

After step S84, the control unit 12 determines whether or not the processing of step S84 has been performed a prescribed number of times (step S85). As the prescribed number of times, a value of 2 or more is set. The prescribed number of times is preferably set to 3 in consideration of reduction of time necessary for the determination of the optimal pitch angle and the determination accuracy of the optimal pitch angle.

When it is determined as NO in step S85, the processing of step S83 and step S84 is performed again. When it is determined as YES in step S85, the control unit 12 determines the current pitch angle as the optimal pitch angle (step S86).

Figure 13:
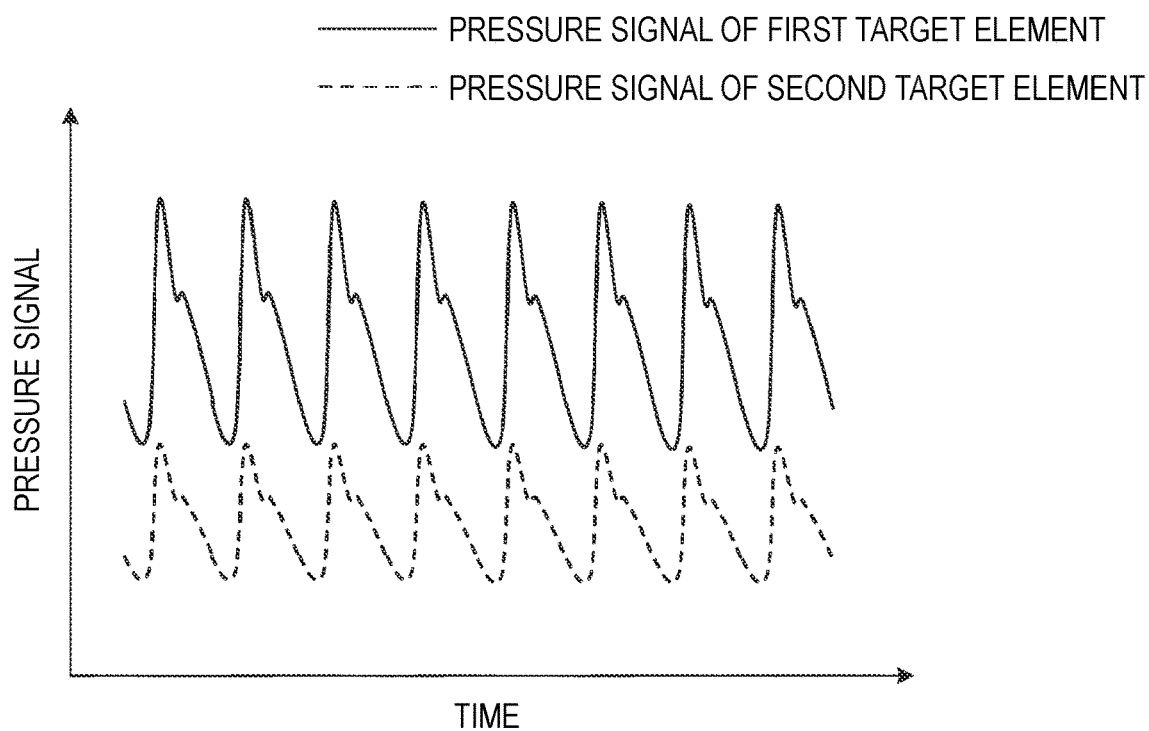
FIG. 13 is a diagram illustrating exemplified pressure signals detected by a first target element and a second target element.
Figure 14:
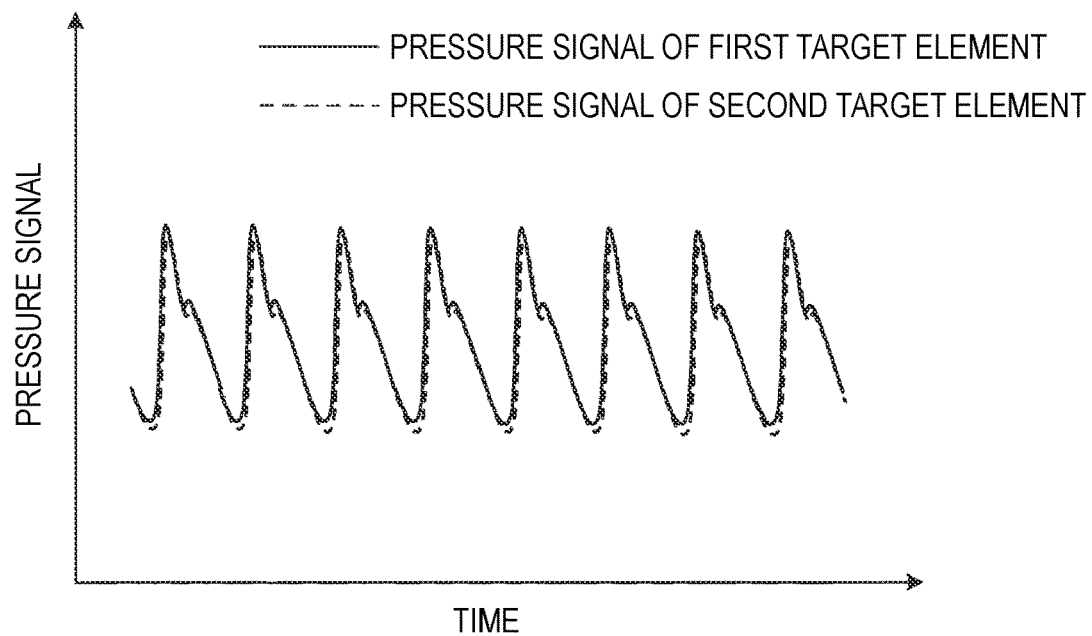
FIG. 14 is a diagram illustrating exemplified pressure signals detected by the first target element and the second target element.

FIG. 13 and FIG. 14 are diagrams illustrating examples of the pressure signals detected by the first target element and the second target element. As illustrated in FIG. 13, when the DC level of the pressure signal detected by the second target element is lower than the DC level of the pressure signal detected by the first target element, the pitch rotation is performed in the direction where the element row 70 comes closer to the body surface (in the negative direction). When the pitch rotation is repeated, a state in which the two DC levels are close to each other as illustrated in FIG. 14 can be obtained.

Through the processing of step S8, the DC levels of the pressure signals detected by the first target element positioned above the radial artery T in the element row 60 and the second target element positioned above the radial artery T in the element row 70 become close to each other, and the optimal pitch angle realizing a state where the radial artery T can be pressed similarly by the element row 60 and the element row 70 can be determined.

Incidentally, the control unit 12 may calculate a first average value of the DC levels of the pressure signals detected by the pressure detecting elements 6a of the element row 60 in step S81, calculate a second average value of the DC levels of the pressure signals detected by the pressure detecting elements 7a of the element row 70 in step S82, and determine the pitch rotation direction in step S83 by using the first average value instead of the peripheral-side DC level and using the second average value instead of the center-side DC level. The optimal pitch angle can be also determined in this manner.

Alternatively, the control unit 12 can determine the optimal pitch angle in step S8 as follows.

After performing the processing of step S81 and step S82 illustrated in FIG. 12, the control unit 12 successively controls the pitch angle to all the settable values for calculating a difference between the peripheral-side DC level and the center-side DC level obtained in a state where the pitch angle is controlled to each of the values, and stores, in the RAM, the calculated difference in association with the pitch angle currently employed by control.

Then, the control unit 12 determines, among the pitch angles thus stored in the RAM, a pitch angle having the smallest difference stored in association as the optimal pitch angle.

According to this modification, a pitch angle obtained in a state where the DC levels of the pressure signals detected by the first target element and the second target element are the closest is determined as the optimal pitch angle.

According to this modification, the control unit 12 may calculate an average value of the DC levels of the pressure signals detected by the pressure detecting elements 6a of the element row 60 in step S81, calculate an average value of the DC levels of the pressure signals detected by the pressure detecting elements 7a of the element row 70 in step S82, and calculate and store a difference of these two average values instead of the difference between the peripheral-side DC level and the center-side DC level.

Alternatively, the control unit 12 may determine, in step S8, the optimal pitch angle based on the AC levels of the pressure signals detected by the pressure detecting elements included in the element row 60 and the element row 70 by a method described in Patent Literature 1.

Referring to FIG. 6 again, after determining the optimal pitch angle in step S8, the control unit 12 controls the pitch angle of the sensor section 6 to the optimal pitch angle determined in step S8 (step S9).

Incidentally, in the exemplified processing of step S8 illustrated in FIG. 12, the determination of the optimal pitch angle in step S86 and the processing of step S9 are simultaneously performed.

Next, the control unit 12 reduces the pressing force applied by the air bag 2 to a reset value (a value $HDP_{RESET}$ illustrated in FIG. 8) smaller than the second pressing value held in step S7 and larger than 0 (zero), and holds the pressing force at the reset value (step S10).

The control unit 12 obtains, in this state, the temperature information detected by the temperature detecting section 7, calculates a difference between the obtained temperature information and the temperature information obtained in step S1, and determines whether or not the difference is equal to or more than a temperature threshold value (step S11).

When it is determined that the difference is less than the temperature threshold value, namely, it is determined that there is no large difference in the temperature of the sensor section 6 between the time of the processing of step S1 and the current time (step S11: NO), the control unit 12 performs processing of step S14.

When it is determined that the difference is equal to or more than the temperature threshold value, namely, it is determined that there is a large difference in the temperature of the sensor section 6 between the time of the processing of step S1 and the current time (step S11: YES), the control unit 12 controls the pressing force to 0 (zero) (step S12), and thereafter, re-sets the reference level of the pressure signal detected by each pressure detecting element of the sensor section 6 based on the current temperature information (step S13). After step S13, the processing of step S14 and following steps is started.

In step S14, the control unit 12 increases the pressing force from the current value to a preliminarily determined value sufficient for occluding the radial artery T (from time t8 to time t9 of FIG. 8).

The control unit 12 controls a rate of increasing the pressing force in step S14 to a lower rate than a rate of increasing the pressing force in step S2, which does not limit the invention.

Incidentally, the processing of step S11 to step S13 of FIG. 6 is not indispensable but can be omitted. In this case, the processing of step S14 follows step S10.

The control unit 12 stores, in the memory 15, the pressure signals detected by the pressure detecting elements of the sensor section 6 during the increase of the pressing force started in step S14, and based on the pressure signals thus stored, determines an optimal pressure detecting element out of all the pressure detecting elements 6a and 7a.

The control unit 12 determines, for example, a pressure detecting element having detected a pressure signal having the maximum AC level during the increase of the pressing force as the optimal pressure detecting element. Besides, the control unit 12 determines, as an optimal pressing force, a pressing force applied when this pressure signal is detected (step S15).

After step S15, the control unit 12 generates pulse wave envelope data based on the pressure signals detected by the optimal pressure detecting element during the increase of the pressing force and stored in the memory 15.

The pulse wave envelope data is data in which the pressing force of the sensor section 6 (the internal pressure of the air bag 2) is in association with the AC level of the pressure signal detected by the optimal pressure detecting element with the optimal pressure detecting element pressed against the body surface with that pressing force.

Then, the control unit 12 calculates the SBP and the DBP based on the thus generated pulse wave envelope data, and generates the correction data to be used in continuous blood pressure measurement of step S18 based on the pressure signals detected by the optimal pressure detecting element during the increase of the pressing force started in step S14 and the calculated SBP and DBP, and stores the correction data in the memory 15 (step S16).

Thereafter, the control unit 12 holds the pressing force at the optimal pressing force determined in step S15 (step S17, time t10 of FIG. 8).

Then, the control unit 12 successively stores, in the memory 15, the pressure signals detected by the optimal pressure detecting element determined in step S15, and based on the AC levels of the pressure signals thus stored and the correction data generated in step S16, calculates the SBP and the DBP every heart rate and stores these in the memory 15 (step S18). The control unit 12 displays the calculated SBP and DBP in, for example, the display section 13 to inform the user.

The control unit 12 repeatedly performs the processing of step S18 until an instruction to stop the blood pressure measurement is issued, and when the stop instruction is issued, the blood pressure measurement processing is ended.

As described so far, the vital information measuring device of the present embodiment determines the optimal roll angle in step S5, and determines the optimal pitch angle in step S8 with the roll angle of the sensor section 6 controlled to the optimal roll angle.

In this manner, through the procedures of determining the optimal roll angle and determining the optimal pitch angle in the state where the roll angle is controlled to the determined optimal roll angle, the optimal pitch angle can be determined with reducing the influence of the pressure from a hard tissue such as a bone or a tendon on the detection accuracy of the pulse wave.

At the time of obtaining a pressure signal necessary for generating the correction data and at the time of the continuous blood pressure measurement, in order to increase the detection accuracy of the pulse wave, an ideal pressing state where the pressing state of the radial artery T by the element row 60 is substantially equivalent to the pressing state of the radial artery T by the element row 70 is preferably obtained. The processing of step S8 is processing for determining the optimal pitch angle for realizing this ideal pressing state.

According to the vital information measuring device of the present embodiment, in the state where the roll angle is controlled to the optimal roll angle at which a signal level derived from a pressure from a hard tissue such as a bone or a tendon is low, the optimal pitch angle for realizing the ideal pressing state can be determined.

Therefore, the determination of the optimal pitch angle for obtaining the ideal pressing state can be performed highly accurately. As a result, the detection accuracy of the pulse wave detected through the processing of step S14 and following steps can be improved to improve the measurement accuracy of the vital information.

Besides, in the vital information measuring device of the present embodiment, the pressing force (the second pressing value) applied in determining the optimal pitch angle in step S8 is set to be smaller than the pressing force (the first pressing value) applied in determining the optimal roll angle in step S5.

When the second pressing value is set to be smaller than the first pressing value in this manner, the optimal pitch angle can be determined in a state where the radial artery T is appropriately pressed, and the determination accuracy of the optimal pitch angle can be improved.

The state where the radial artery T is appropriately pressed refers to a state where the radial artery T is not occluded and the pressed surface of the radial artery T is flat and influence of tone is negligible, namely, what is called a tonometry state.

In the exemplified operation illustrated in FIG. 6, the pressing force is held, in step S7, at the pressing force ($HDP_{ACmax}$) with which the AC level of the target element of the selected element row can be the maximum value ($AC_{max}$). The state where the pressing force is held at $HDP_{ACmax}$ is regarded to be the closest to the tonometry state. Therefore, when the second pressing value is set to $HDP_{ACmax}$, the determination accuracy of the optimal pitch angle can be improved.

Incidentally, the second pressing value is set to $HDP_{ACmax}$ in the exemplified operation illustrated in FIG. 6, which does not limit the present invention. The second pressing value may be an arbitrary value corresponding to a range of the pressing force where change of the DC level of the target element determined at each time in the selected element row is equal to or less than a change threshold value. A pressing force with which the change of the DC level of the target element is the smallest is substantially equal to a pressing force with which the AC level of the target element is the maximum.

In other words, the second pressing value may be set to a value in the vicinity of the pressing force with which the AC level of the target element determined at each time in the selected element row is the maximum.

Specifically, the second pressing value is preferably set to an arbitrary numerical value corresponding to a range of the pressing force with which the AC level of the target element determined at each time in the selected element row is as high as 0.9 times or more of the maximum value ($AC_{max}$ illustrated in FIG. 8), and is more preferably set to an arbitrary numerical value corresponding to a range of the pressing force with which it is as high as 0.95 times or more of the maximum value.

The state where the pressing force is held at $HDP_{ACmax}$ is regarded to be the closest to the tonometry state. Therefore, the second pressing value is most preferably set to $HDP_{ACmax}$ as in the exemplified operation of FIG. 6.

Besides, according to the vital information measuring device of the present embodiment, either one of the element row 60 and the element row 70 is selected as the selected element row in step S3. Then, the optimal roll angle is determined based on the pressure signals detected by the plural pressure detecting elements of the one selected element row.

Specifically, the control unit 12 selects an element row that has priorly occluded the radial artery T as the selected element row in step S3, and determines the optimal roll angle in the state where the pressing force is held at the pressing force applied when the selected element row occluded the radial artery T.

Owing to this configuration, the optimal roll angle can be determined based on the pressure signals output from an element row not affected by blood flow change or the like caused by the occlusion of the radial artery T. In other words, the pressure signal output from the selected element row can be improved in the reliability, and the determination accuracy of the optimal roll angle can be improved.

Besides, since the element row that has been able to occlude the radial artery T in a shorter period of time is selected as the selected element row, time necessary for the determination of the optimal roll angle can be reduced to reduce time required for starting the blood pressure measurement.

Furthermore, in the vital information measuring device of the present embodiment, the optimal roll angle is determined based on the DC levels of the pressure signals detected by the pressure detecting elements of either one of the element rows 60 and 70. Since the optimal roll angle is thus determined based on the DC levels of the pressure signals, the roll angle minimally affected by a pressure from a hard tissue such as a bone or a tendon can be highly accurately determined.

Incidentally, the control unit 12 may determine, in step S5, the optimal roll angle based on the absolute values of the pressure signals detected by the pressure detecting elements of the selected element row instead of the DC levels of the pressure signals detected by the pressure detecting elements of the selected element row.

The state where the pressing force is held at the first pressing value in step S4 is a state where the radial artery T is occluded by the selected element row. In other words, in this state, the AC levels of the pressure signals detected by the pressure detecting elements of the selected element row are sufficiently low.

Therefore, even when the optimal roll angle is determined based on the absolute values of the pressure signals detected by the plural pressure detecting elements of the selected element row, the influence of the pressure from a hard tissue such as a bone or a tendon can be reduced with given accuracy. When the DC levels are used as described above, a distribution of the pressure from a hard tissue such as a bone or a tendon can be more accurately detected, and hence the determination accuracy of the optimal roll angle can be improved.

Besides, in the vital information measuring device of the present embodiment, the optimal pitch angle is determined based on the DC levels of the pressure signals detected by the plural pressure detecting elements included in each of the element rows 60 and 70. Since the optimal pitch angle is thus determined based on the DC levels of the pressure signals, the optimal pitch angle with which the ideal pressing state can be realized can be highly accurately determined. The reason is as follows.

In the vital information measuring device of the present embodiment, the element row 60 and the element row 70 press different portions of a living body. Besides, when the radial artery T is started to be occluded on the peripheral side having high resistance prior to the center side, a reflected wave is caused accordingly. The reflected wave is superimposed on a pressure signal detected by a pressure detecting element of the element row 70 positioned above the radial artery T.

In this manner, due to a difference in the composition of a subcutaneous tissue of the pressed portion of the living body, and the occurrence of a reflected wave and the like, even in the ideal pressing state, the AC level of a pressure signal detected by a pressure detecting element of the element 60 positioned above the radial artery T may be different from the AC level of a pressure signal detected by a pressure detecting element of the element row 70 positioned above the radial artery T in some cases.

On the other hand, the DC level of the pressure signal detected by the pressure detecting element of the element row 60 positioned above the radial artery T and the DC level of the pressure signal detected by the pressure detecting element of the element row 70 positioned above the radial artery T are not affected by the difference in the composition of the subcutaneous tissue of the pressed portion of the living body, and the occurrence of a reflected wave and the like.

Therefore, when the optimal pitch angle is determined based on the DC levels of the pressure signals detected by the plural pressure detecting elements included in each of the element rows 60 and 70, the optimal pitch angle can be highly accurately determined.

Incidentally, also when the optimal pitch angle is determined based on the AC levels of the pressure signals detected by the plural pressure detecting elements included in each of the element rows 60 and 70, the optimal pitch angle can be determined with given accuracy.

Furthermore, in the vital information measuring device of the present embodiment, the optimal pitch angle can be determined based on pressure signals respectively detected by two pressure detecting elements, that is, one pressure detecting element selected from the element row 60 and one pressure detecting element selected from the element row 70.

When the optimal pitch angle is thus determined based on the pressure signals of the two pressure detecting elements, the computational complexity necessary for determining the optimal pitch angle can be reduced, so as to reduce the power consumption and reduce the time required for starting the blood pressure measurement.

Incidentally, in the exemplified processing of FIG. 12, one element is selected, in step S81 and step S82, from the target elements determined through the processing of step S30 to step S37 of FIG. 7. When one to be used for determining the optimal pitch angle is thus selected from the target elements preliminarily determined, the computational complexity necessary for determining the optimal pitch angle can be reduced. As a result, the power consumption can be reduced, and the time required for starting the blood pressure measurement can be reduced.

Besides, in the vital information measuring device of the present embodiment, after determining the optimal pitch angle, the pressing force is reduced to the reset value smaller than the second pressing value and larger than 0 (zero), and thereafter, the processing of step S14 and following steps is performed. When the processing of step S14 and following steps is thus performed without reducing the pressing force to 0 (zero), the time required for starting the blood pressure measurement can be reduced.

Furthermore, when the processing of step S14 and following steps is performed with the pressing force once reduced, the optimal pressing force and the optimal pressure detecting element can be determined with the sensor section 6 controlled to the optimal roll angle and the optimal pitch angle, and hence the detection accuracy of the pulse wave can be improved.

Besides, the vital information measuring device of the present embodiment re-sets, after determining the optimal pitch angle, the reference level of each pressure detecting element of the sensor section 6 with the pressing force reduced to 0 (zero) when there has arisen a large difference between the temperature information obtained at the initial state and the current temperature information. When the reference revel is thus re-set, the detection accuracy of the pulse wave in the processing of step S14 and following steps can be improved.

Furthermore, in the vital information measuring device of the present embodiment, the rate of increasing the pressing force in step S2 is higher than the rate of increasing the pressing force in step S14.

Owing to this structure, the increase of the pressing force necessary for determining the optimal roll angle and the optimal pitch angle can be rapidly performed, and the time required for starting the blood pressure measurement can be reduced. On the other hand, since the rate of increasing the pressing force necessary for generating the correction data is relatively low, the correction data can be highly accurately obtained.

In the vital information measuring device of the present embodiment, before determining the optimal roll angle in step S5, the control unit 12 may pitch-rotates the sensor section 6 so as to obtain a good detection state of a pressure signal of each of the element row 60 and the element row 70.

For example, after starting the increase of the pressing force in step S2, the control unit 12 compares, at regular timing until the processing of step S38 of FIG. 7 is performed, the AC level of the pressure signal of the latest first target element stored in the RAM with the AC level of the pressure signal of the latest second target element, and determines, based on a result of the comparison, whether or not the pitch rotation is necessary.

When a difference between the two AC levels is equal to or more than a threshold value, the control unit 12 determines that the radial artery T is not satisfactorily flattened by the element row including a target element having a relatively lower AC level, and determines that the pitch rotation is necessary. Then, the sensor section 6 is pitch-rotated in a direction in which this element row of interest comes closer to the body surface. The rotation amount at this point is arbitrary, and may be set to, for example, a controllable minimum value.

When the difference between the two AC levels is less than the threshold value, the control unit 12 determines that the two element rows respectively satisfactorily flatten the radial artery T, and determines that there is no need of the pitch rotation.

For example, when the AC level of the latest first target element is higher than the AC level of the latest second target element by the threshold value or more at the above-described timing, the control unit 12 pitch-rotates the sensor section 6 in the negative direction.

Thus, the AC level of the second target element can be increased. As a result, as compared with a case where the pitch rotation is not performed, a possibility of the element row 70 selected as the selected element row can be increased, and hence, choices of the element rows usable for the determination of the optimal pitch angle can be increased.

Figure 15:
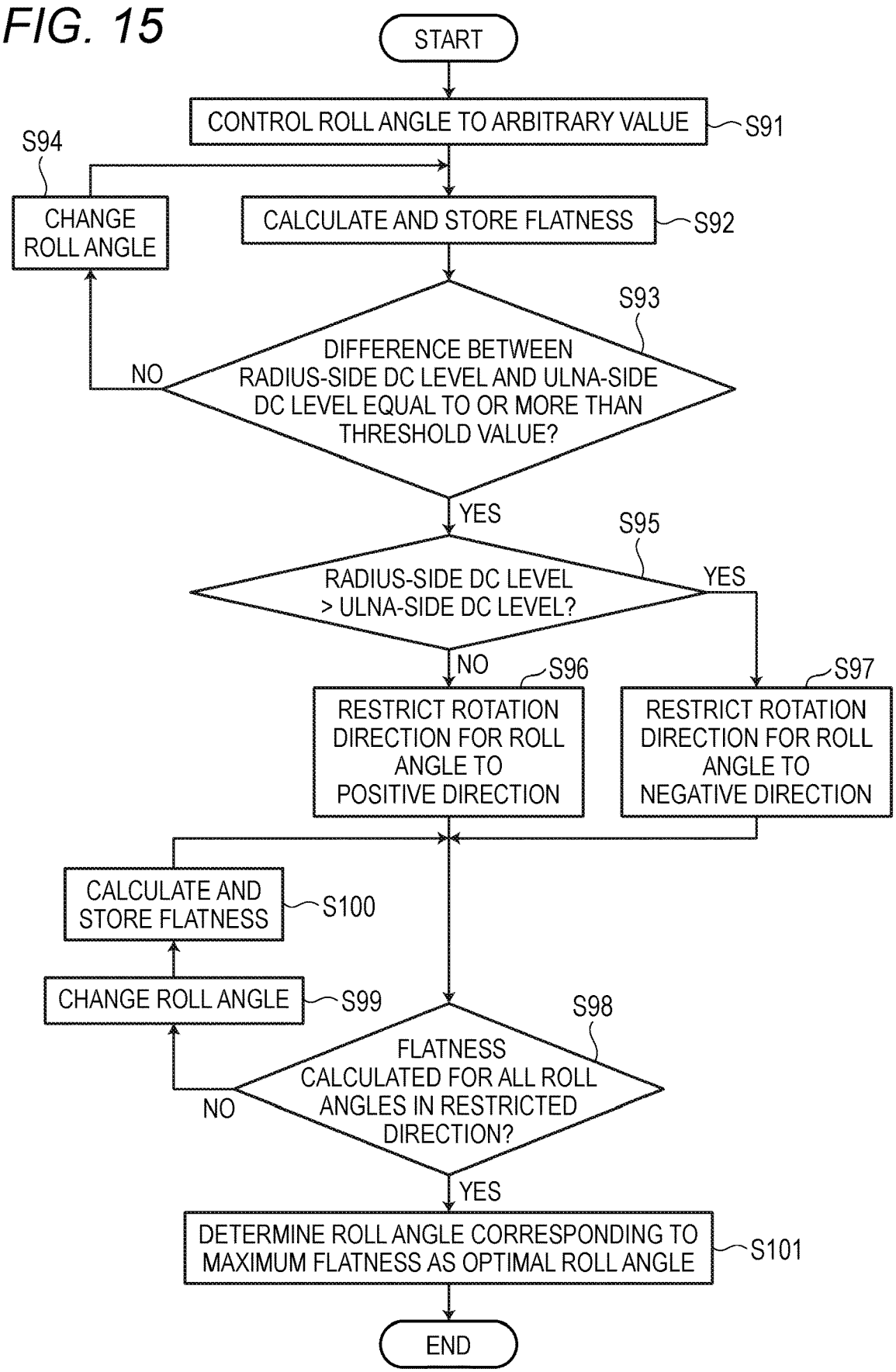
FIG. 15 is a flowchart used for explaining a modification of detailed processing of step S5 of FIG. 6.

FIG. 15 is a flowchart illustrating a modification of the detailed processing of step S5 of FIG. 6.

First, the control unit 12 controls the rotation drive section 10 to control the roll angle to an arbitrary angle (step S91).

Next, the control unit 12 obtains the DC levels of pressure signals respectively detected by the first pressure detecting element to the third pressure detecting element among the respective pressure detecting elements of the selected element row, calculates the flatness in the same manner as in the processing of step S53 based on the three DC levels thus obtained, and stores the flatness in the RAM in association with the roll angle currently employed by control (step S92).

Next, the control unit 12 determines whether or not a difference between the DC level of the pressure signal detected by the second pressure detecting element (hereinafter referred to as the radius-side DC level) and the DC level of the pressure signal detected by the third pressure detecting element (hereinafter referred to as the ulna-side DC level) is equal to or more than a threshold value (step S93).

When the difference between the radius-side DC level and the ulna-side DC level is less than the threshold value (step S93: NO), the control unit 12 controls the rotation drive section 10 to roll-rotate the sensor section 6 by a minimum angle in the positive direction or the negative direction (step S94), and thereafter, returns the processing to step S92.

When the difference between the radius-side DC level and the ulna-side DC level is equal to or more than the threshold value (step S93: YES), the control unit 12 determines whether or not the radius-aide DC level is higher than the ulna-side DC level (step S95).

When the radius-side DC level is lower than the ulna-side DC level (step S95: NO), the control unit 12 restricts the direction of the roll rotation to the positive direction (the counterclockwise direction taken from the side of the left elbow) (step S96). In other words, the control unit 12 excludes, from candidates of the optimal roll angle, roll angles toward the negative direction from the current roll angle out of roll angles excluding roll angles having been calculated for the flatness.

When the radius-side DC level is higher than the ulna-side DC level (step S95: YES), the control unit 12 restricts the direction of the roll rotation to the negative direction (the clockwise direction taken from the side of the left elbow) (step S97). In other words, the control unit 12 excludes, from the candidates of the optimal roll angle, roll angles toward the positive direction from the current roll angle out of the roll angles excluding the roll angles having been calculated for the flatness.

After step S96 and step S97, the control unit 12 determines whether or not the flatness has been calculated for all angles in the rotation direction restricted based on the current roll angle as described above out of all the settable roll angles (step S98).

When it is determined as NO in step S98, the control unit 12 controls the rotation drive section 10 to control the sensor section 6 to a roll angle not calculated for the flatness yet among the settable roll angles in the restricted rotation direction (step S99).

Then, the control unit 12 obtains the DC levels of the pressure signals respectively detected by the first pressure detecting element to the third pressure detecting element, calculates the flatness in the same manner as in the processing of step S52 based on the obtained three DC levels, and stores the flatness in the RAM in association with the roll angle currently employed by control (step S100). After step S100, the processing returns to step S98.

When it is determined as YES in step S98, the control unit 12 determines, as the optimal roll angle, a roll angle in association with the largest flatness out of the roll angles stored in the RAM through the processing of step S92 and step S100 (step S101).

In this manner, according to the modification illustrated in FIG. 15, as compared with the exemplified processing illustrated in FIG. 9, the number of roll angles to be calculated for the flatness can be reduced. Therefore, the computation complexity for determining the optimal roll angle can be reduced, and the power consumption caused in the roll rotation can be reduced.

Incidentally, it is assumed here that the angles settable as the roll angle are three angles of 0 (zero) degree, +θ1 degrees and −θ1 degrees (wherein θ1 is an arbitrary value), and that the arbitrary value used in step S91 is 0 (zero) degree.

In this case, when the processing of the initial step S93 is determined as YES and step S95 is determined as NO, the control unit 12 determines +θ1 degrees as the optimal roll angle. Alternatively, when the processing of the initial step S93 is determined as YES and step S95 is determined as YES, the control unit 12 determines −θ1 degrees as the optimal roll angle.

In this manner, according to this modification, the optimal roll angle can be also determined without performing the roll rotation.

Although the rotation section 5 is configured to be rotatable about each of the first axis X and the second axis Y in the vital information measuring device of the present embodiment, the rotation section 5 may be configured to be rotatable about either one of the first axis X and the second axis Y.

When the rotation section 5 is configured to be rotatable about merely the first axis X (configured to be capable of the pitch rotation alone), the control unit 12 may omit the processing of step S5 and step S6 in the flowchart of FIG. 6 so as to perform the processing of step S7 and following steps after the processing of step S4.

Besides, when the rotation section 5 is configured to be rotatable about merely the first axis X, each of the element row 60 and the element row 70 of the sensor section 6 need not include a plurality of pressure detecting elements, and may be configured to include at least one pressure detecting element. In other words, the sensor section 6 may be configured to include at least one pair of pressure detecting elements of the pressure detecting element 6a and the pressure detecting element 7a arranged in the direction A. In addition, in a case that three or more element rows are arranged in the direction A, the pair consists of the pressure detecting element included in one of the two element rows among the three or more element rows and the pressure detecting element included in the other of the two element rows.

In this configuration, the first target element described with reference to FIG. 7 is always the same pressure detecting element 6a, and the second target element is always the same pressure detecting element 7a. Besides, in step S38, the pressure detecting element whose AC level has reached in advance the occlusion completion determination threshold value is selected.

Besides, in step S39, a pressing force applied at the time when the AC level of the selected pressure detecting element has reached the occlusion completion determination threshold value is set as the first pressing value. Furthermore, in step S40, a pressing force applied at the time when the AC level of the selected pressure detecting element has reached a peak is set as the second pressing value.

Furthermore, in step S8, the control unit 12 omits step S81 and step S82 of FIG. 12, and in step S83, compares the DC levels of the pressure signals respectively detected by the pressure detecting element 6a and the pressure detecting element 7a to set the rotation direction and the rotation amount of the pitch rotation of the sensor section 6 based on the result of the comparison and the current pitch angle.

When the rotation section 5 is configured to be rotatable about merely the second axis Y (configured to be capable of the roll rotation alone), the control unit 12 may omit the processing of step S7 to step S9 in the flowchart of FIG. 6 so as to perform the processing of step S10 and following steps after the processing of step S6.

Besides, when the rotation section 5 is configured to be rotatable about merely the second axis Y, either one of the element row 60 and the element row 70 may be omitted in the sensor section 6.

For example, when the sensor section 6 is configured to include the element row 60 alone, step S34 to step S38 are omitted in FIG. 7, and when it is determined as YES in step S33, the processing of step S39 and following steps is performed in the operation. Besides, the selected element row used in step S39 and following steps is the element row 60.

It should be understood that the present embodiment herein disclosed is merely illustrative and not restrictive. The scope of the present invention is not limited to the above description but is defined by appended claims, and it is intended that equivalents to the appended claims and all changes made within the scope thereof are embraced.

For example, the wrist-worn vital information measuring device for detecting a pulse wave from the radial artery of a wrist has been described so far, but the present invention may be applied to a device for detecting a pulse wave from the carotid artery or the dorsalis pedis artery.

Besides, the sensor section 6 may be configured to include three or more element rows arranged in the direction A.

In the case of employing this configuration, the control unit 12 selects, in step S3 of FIG. 6, an element row having occluded the radial artery T most early among the three or more element rows as the selected element row. Alternatively, the control unit 12 preliminarily selects any one of the three or more element rows as the selected element row.

Besides, in step S8 of FIG. 6, the control unit 12 determines the optimal pitch angle with which the DC levels or the AC levels of pressure signals detected by one pressure detecting element selected from each of the three or more element rows are close to one another.

As described so far, the followings are herein disclosed:

A pulse wave detecting device herein disclosed includes: a sensor section that includes at least one pair of pressure detecting elements arranged in a direction perpendicular to a first direction; a pressing section that presses the sensor section against a body surface of a living body in a state where the first direction crosses a direction of an artery extending below the body surface; a rotation drive section that rotates the sensor section about an axis extending in the first direction; a storage control section that stores, in a storage medium, pressure signals detected by the pressure detecting elements in a state where a rotation angle of the sensor section about the axis is controlled to a specific value and the sensor section is pressed against the body surface by the pressing section; and a rotation angle determining section that determines the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

In the pulse wave detecting device herein disclosed, the rotation angle determining section determines, as the specific value, a value of the rotation angle with which a difference between the DC component of the pressure signal detected by the first pressure detecting element and the DC component of the pressure signal detected by the second pressure detecting element is the minimum.

In the pulse wave detecting device herein disclosed, the sensor section includes two element rows each including a plurality of pressure detecting elements arranged in the first direction, the two element rows being arranged in the direction perpendicular to the first direction, pressure detecting elements disposed in the same position in the first direction respectively in the two element rows together form the pair, and the rotation angle determining section selects, as the first pressure detecting element, one of the plurality of pressure detecting elements included in a first element row out of the two element rows based on a group of pressure signals detected by the pressure detecting elements of the first element row, and selects, as the second pressure detecting element, one of the plurality of pressure detecting elements included in a second element row out of the two element rows based on a group of pressure signals detected by the pressure detecting elements of the second element row.

In the pulse wave detecting device herein disclosed, the rotation angle determining section performs processing for successively determining, as a target element, one element positioned on the artery from the pressure detecting elements included in the element rows based on a group of pressure signals detected by the respective pressure detecting elements of the element rows during increase of a pressing force applied to the sensor section against the body surface by the pressing section, and determines the specific value in a state where the sensor section is pressed against the body surface with a specific pressing force with which variation of a DC component of a pressure signal detected by the target element successively determined in one element row out of the two element rows is equal to or lower than a threshold value.

In the pulse wave detecting device herein disclosed, the rotation angle determining section performs processing for successively determining, as a target element, one element positioned on the artery from the pressure detecting elements included in the element rows based on a group of pressure signals detected by the respective pressure detecting elements of the element rows during increase of a pressing force applied to the sensor section against the body surface by the pressing section, and determines the specific value in a state where the sensor section is pressed against the body surface with an arbitrary specific pressing force with which an AC component of a pressure signal detected by the target element successively determining in one element row out of the two element rows has a value as large as 0.9 times or more of a maximum value of the AC component.

In the pulse wave detecting device herein disclosed, the rotation angle determining section defines, as the first pressure detecting element and the second pressure detecting element, target elements respectively determined from the two element rows in a state where the pressing force is the specific pressing force during the increase.

A vital information measuring device herein disclosed includes: the above described pulse wave detecting device; and a vital information calculating section that calculates vital information based on the pressure signals stored in the storage medium.

A method for controlling a pulse wave detecting device herein disclosed is a method for controlling a pulse wave detecting device including: a sensor section that includes at least one pair of pressure detecting elements arranged in a direction perpendicular to a first direction; a pressing section that presses the sensor section against a body surface of a living body in a state where the first direction crosses a direction of an artery extending below the body surface; and a rotation drive section that rotates the sensor section about an axis extending in the first direction, the method includes: a storage control step of storing, in a storage medium, pressure signals detected by the pressure detecting elements in a state where a rotation angle of the sensor section about the axis is controlled to a specific value and the sensor section is pressed against the body surface by the pressing section; and a rotation angle determining step of determining the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

A control program for a pulse wave detecting device herein disclosed is a control program for a pulse wave detecting device including: a sensor section that includes at least one pair of pressure detecting elements arranged in a direction perpendicular to a first direction; a pressing section that presses the sensor section against a body surface of a living body in a state where the first direction crosses a direction of an artery extending below the body surface; and a rotation drive section that rotates the sensor section about an axis extending in the first direction, the control program causes a computer to execute: a storage control step of storing, in a storage medium, pressure signals detected by the pressure detecting elements in a state where a rotation angle of the sensor section about the axis is controlled to a specific value and the sensor section is pressed against the body surface by the pressing section; and a rotation angle determining step of determining the specific value based on DC components of pressure signals detected, in a state where the sensor section is pressed against the body surface by the pressing section, respectively by a first pressure detecting element and a second pressure detecting element out of the pressure detecting elements included in the sensor section, the first pressure detecting element and the second pressure detecting element being different from each other in a position in the direction perpendicular to the first direction.

The present invention is highly conveniently and effectively applied to a sphygmomanometer in particular.

According to the present invention, a pulse wave detecting device capable improving pulse wave detection accuracy by flexibly changing a pressing state, toward a body surface, of a sensor section pressed against the body surface for use, a vital information measuring device, a control method for a pulse wave detecting device, and a control program for a pulse wave detecting device can be provided.

The present invention has been described so far with reference to a specific embodiment, and it is noted that the present invention is not limited to the embodiment but can be variously modified without departing from the technical spirit of the present invention disclosed herein.

What is claimed is:

1. A pulse wave detecting device, comprising:
   a sensor section that includes at least one pair of pressure detecting elements arranged in a direction perpendicular to a first direction;
   a pressing section that is configured to press the sensor section against a body surface of a living body with the first direction crossing a direction of an artery extending below the body surface;
   a rotation drive section that rotates the sensor section about an axis extending in the first direction;
   a storage control section that stores, in a storage medium, pressure signals detected by the pressure detecting elements with a rotation angle of the sensor section about the axis controlled to a specific value and with the sensor section pressed by the pressing section; and
   a rotation angle determining section that determines the specific value based on DC components of pressure signals detected, with the sensor section pressed by the pressing section, respectively by a first pressure detecting element and a second pressure detecting element out of the pressure detecting elements included in the sensor section, the first pressure detecting element and the second pressure detecting element being different from each other in position in the direction perpendicular to the first direction.

2. The pulse wave detecting device according to claim 1, wherein the rotation angle determining section determines, as the specific value, a value of the rotation angle with which a difference between the DC component of the pressure signal detected by the first pressure detecting element and the DC component of the pressure signal detected by the second pressure detecting element is a minimum.

3. The pulse wave detecting device according to claim 1, wherein the sensor section includes two element rows each including a plurality of pressure detecting elements arranged in the first direction, the two element rows being arranged in the direction perpendicular to the first direction,
   wherein pressure detecting elements disposed adjacent to each other in the first direction respectively in the two element rows together form a pair, and
   wherein the rotation angle determining section selects, as the first pressure detecting element, one of the plurality of pressure detecting elements included in a first element row out of the two element rows based on a group of pressure signals detected by the pressure detecting elements of the first element row, and selects, as the second pressure detecting element, one of the plurality of pressure detecting elements included in a second element row out of the two element rows based on a group of pressure signals detected by the pressure detecting elements of the second element row.

4. The pulse wave detecting device according to claim 3, wherein the rotation angle determining section performs processing for successively determining, as a target element, one element to be positioned on the artery from the pressure detecting elements included in the element rows based on a group of pressure signals detected by the respective pressure detecting elements of the element rows during an increase of a pressing force applied to the sensor section by the pressing section, and determines the specific value with the sensor section pressed by a specific pressing force with which variation of a DC component of a pressure signal detected by the target element successively determined in one element row out of the two element rows is equal to or lower than a threshold value.

5. The pulse wave detecting device according to claim 3, wherein the rotation angle determining section performs processing for successively determining, as a target element, one element to be positioned on the artery from the pressure detecting elements included in the element rows based on a group of pressure signals detected by the respective pressure detecting elements of the element rows during an increase of a pressing force applied to the sensor section by the pressing section, and determines the specific value with the sensor section pressed by an arbitrary pressing force with which an AC component of a pressure signal detected by the target element successively determining in one element row out of the two element rows has a value as large as 0.9 times or more of a maximum value of the AC component.

6. The pulse wave detecting device according to claim 4, wherein the rotation angle determining section defines, as the first pressure detecting element and the second pressure detecting element, target elements respectively determined from the two element rows with the pressing force being the specific pressing force during the increase.

7. A vital information measuring device, comprising:
   the pulse wave detecting device according to claim 1; and
   a vital information calculating section that calculates vital information based on the pressure signals stored in the storage medium.

8. A method for controlling a pulse wave detecting device, the pulse wave detecting device including: a sensor section that includes at least one pair of pressure detecting elements arranged in a direction perpendicular to a first direction; a pressing section that is configured to press the sensor section against a body surface of a living body with the first direction crossing a direction of an artery extending below the body surface; and a rotation drive section that rotates the sensor section about an axis extending in the first direction, the method comprising:
   a storage control step of storing, in a storage medium, pressure signals detected by the pressure detecting elements with a rotation angle of the sensor section about the axis controlled to a specific value and with the sensor section pressed by the pressing section; and
   a rotation angle determining step of determining the specific value based on DC components of pressure signals detected, with the sensor section pressed by the pressing section, respectively by a first pressure detecting element and a second pressure detecting element out of the pressure detecting elements included in the sensor section, the first pressure detecting element and the second pressure detecting element being different from each other in position in the direction perpendicular to the first direction.

9. A non-transitory computer-readable storage medium, which stores a control program for a pulse wave detecting device, the pulse wave detecting device including: a sensor section that includes at least one pair of pressure detecting elements arranged in a direction perpendicular to a first direction; a pressing section that is configured to press the sensor section against a body surface of a living body with the first direction crossing a direction of an artery extending below the body surface; and a rotation drive section that rotates the sensor section about an axis extending in the first direction, the control program causing a computer to execute:
- a storage control step of storing, in a storage medium, pressure signals detected by the pressure detecting elements with a rotation angle of the sensor section about the axis controlled to a specific value and with the sensor section pressed by the pressing section; and
- a rotation angle determining step of determining the specific value based on DC components of pressure signals detected, with the sensor section pressed by the pressing section, respectively by a first pressure detecting element and a second pressure detecting element out of the pressure detecting elements included in the sensor section, the first pressure detecting element and the second pressure detecting element being different from each other in position in the direction perpendicular to the first direction.

* * * * *